United States Patent [19]
Ullrich

[11] Patent Number: 5,910,309
[45] Date of Patent: Jun. 8, 1999

[54] UV-INDUCED FACTOR FOR IMMUNOSUPPRESSION

[75] Inventor: Stephen E. Ullrich, Houston, Tex.

[73] Assignee: Board Of Regents, The University Of Texas System, Austin, Tex.

[21] Appl. No.: 08/431,471

[22] Filed: May 1, 1995

Related U.S. Application Data

[63] Continuation of application No. 07/987,760, Dec. 8, 1992, abandoned, which is a continuation-in-part of application No. 07/768,232, Oct. 10, 1991, abandoned, which is a continuation of application No. PCT/US90/01402, Mar. 14, 1990, which is a continuation-in-part of application No. 07/323,615, Mar. 14, 1989, abandoned.

[51] Int. Cl.$^6$ .......................... A61K 41/00; A61K 38/19; C07K 14/52
[52] U.S. Cl. ........................... 424/198.1; 514/8; 530/395
[58] Field of Search .............................. 424/198.1; 514/8; 530/395

[56] References Cited

FOREIGN PATENT DOCUMENTS

| PCT/US90/ | | |
|---|---|---|
| 01402 | 7/1990 | European Pat. Off. . |
| WO90/10461 | 9/1990 | WIPO . |

OTHER PUBLICATIONS

Gallo, R. L. et al. Journal of Investigative Dermatology 97 (2): 203–209, Aug. 1991.

Chodakewitz, J. A. et al. Journal of Immunology 144 (6) 2190–2196, Mar. 1990.

Kahan, B. D. Current Opinion in Immunology 4: 553–560, Aug. 1992.

Kripke, "Immunological Unresponsiveness Induced by Ultraviolet Radiation", *Immunol. Rev.*, No. 80 (1984) 87–102, published in Europe.

Kripke et al., "In vivo Immune Responses of Mice During Carcinogenesis by Ultraviolet Irradiation," *J. Natl. Can. Inst.*, vol. 59 (1977) 1227–1230, published in USA.

Noonan et al., "Suppression of Contact Hypersensitivity by Ultraviolet Radiation: An Experimental Model," *Springer Semin. Immunopath.*, vol. 4 (1981) 293–304, published in Europe.

Greene et al., "Impairment of Antigen–Presenting Cell Function by Ultraviolet Radiation," *Proc. Natl. Acad. Sci. U.S.A.*, vol. 76 (1979) 6591–6595, published in USA.

Ullrich et al., "Suppression of the Induction of Delayed–Type Hypersensitivity Reactions in Mice by a Single Exposure to Ultraviolet Radiation," *Photochem. Photobiol.*, vol. 43 (1986) 633–638, published in USA.

Ullrich, "Suppression of the Immune Response to Allogeneic Histocompatibility Antigens by a Single Exposure to Ultraviolet Radiation," *Transplantation*, vol. 42 (1986) 287–291, published in USA.

Molendijk et al., "Suppression of Delayed–Type Hypersensitivity to Histocompatibility Antigens by Ultraviolet Radiation," *Immunology*, vol. 62 (1987) 299–305, published in Europe.

Swartz, "Role of UVB–Induced Serum Factor(s) in Suppression of Contact Hypersensitivity in Mice," *J. Invest. Dermatol.*, vol. 83 (1984) 305–307, published in USA.

Harriott–Smith et al., "Circulating Suppressor Factors in Mice Subjected to Ultraviolet Irradiation and Contact Sensitization," *Immunology*, vol. 57 (1986) 207–211, published in Europe.

DeFabo et al., "Mechanism of Immune Suppression by Ultraviolet Irradiation in vivo, I. Evidence for the Existence of Unique Photoreceptor in Skin and its Role in Photoimmunology," *J. Exp. Med.*, vol. 157 (1983) 84–98, published in USA.

Ross et al., "Ultraviolet–Irradiated Urocanic Acid Suppresses Delayed–Type Hypersensitivity to Herpes Simplex Virus in Mice," *J. Invest. Dermatol.*, vol. 87 (1986) 630–633, published in USA.

Noonan et al., "Cis–Urocanic Acid, a Product Formed by Ultraviolet B Irradiation of the Skin, Initiates an Antigen Presentation Defect in Splenic Dendritic Cells in vivo," *J. Invest. Dermatol.*, vol. 90 (1988) 92–99, published in USA.

Robertson et al., "In vivo Administration of Interleukin 1 to Normal Mice Depresses their Capacity to Elicit Contact Hypersensitivity Responses: Prostaglandins Are Involved in this Modification of Immune Function," *J. Invest. Dermatol.*, vol. 88 (1987) 380–387, published in USA.

Gahring et al., "Effect of Ultraviolet Radiation on the Production of Epidermal Cell Thymocyte–Activating Factor/Interleukin 1 in vivo and in vitro," *Proc. Natl. Acad. Sci. USA*, vol. 81 (1984) 1198–1202, published in USA.

Schwarz et al., "Inhibition of the Induction of Contact Hypersensitivity by a UV–Mediated Epidermal Cytokine," *J. Invest. Dermatol.*, vol. 87 (1986) 289–291, published in USA.

(List continued on next page.)

*Primary Examiner*—Frank C. Eisenschenk
*Assistant Examiner*—Evelyn Rabin
*Attorney, Agent, or Firm*—Arnold, White & Durkee

[57] ABSTRACT

The present invention comprises the method of selectively suppressing an immune response of a mammal to a particular alloantigen. The method includes several steps. One step is administering to a mammal an effective amount of UVB-radiation. It is demonstrated herein UVB radiation selectively suppresses the DTH response in mammals. Epidermal cell cultures, when subjected to UVB irradiation (280 nm to 320 nm) produce a specific immunosuppressive factor. The immunosuppressive factor is reactive with an antibody directed toward IL-10. Another step of the inventive method involves desensitizing a mammal to a particular alloantigen. It has been determined that a mammal will become tolerant to a particular alloantigen once the subject mammal has been irradiated with a pre-determined wavelength of UVR and thereafter sensitized with the particular alloantigen. This may analogously be accomplished using the immunosuppressive factor from in vitro epidermal cell cultures of the present invention.

6 Claims, 8 Drawing Sheets

OTHER PUBLICATIONS

Fisher et al., "Suppressor T Lymphocytes Control the Development of Primary Skin Cancers in Ultraviolet–Irradiated Mice," *Science*, vol. 216 (1982) 1133–1134, published in USA.

Lau et al., "Pancreatic Islet Allograft Prolongation by Donor–Specific Blood Transfusions Treated with Ultraviolet Irradiation," *Science*, vol. 221 (1983) 754–756, published in USA.

Lau et al., "Prolongation Rat Islet Allograft Survival by Direct Ultraviolet Irradiation of the Graft," *Science*, vol. 223 (1984) 607–609, published in USA.

Yuspa et al., "A Survey of Transformation Markers in Differentiating Epidermal Cell Lines in Culture," *Cancer Research*, vol. 40 (1980) 4694–4703, published in USA.

Shearer, "Cell–Mediated Cytotoxicity to Trinitrophenyl–Modified Syngeneic Lymphocytes," *Eur. J. Immunol.*, vol. 4 (1974) 527–533, published in Europe.

Mishell et al., "Immunization of Dissociated Spleen Cell Cultures from Normal Mice," *J. Expo. Med.*, vol. 126 (1967) 423–442, published in USA.

Jerne et al., "Plaque Formation in Agar by Single Antibody Producing Cells," *Science*, vol. 140 (1963) 405, published in USA.

Dunnett, "A Multiple Comparison Procedure for Comparing Several Treatments with a Control," *J. Am. Stat. Assoc.*, vol. 50 (1955) 1096–1121, published in USA.

Storb, "Critical Issues in Bone Marrow Transplantation," *Transplantation Proc.*, vol. 19 (1987) 2774–2781, published in USA.

Klein et al., "Participation of H–2 Regions in Heart–Transplant Rejection," *Transplantation*, vol. 22 (1976) 384–390, published in USA.

Korngold et al., "Surface Markers of T Cells Causing Lethal Graft vs. Host Disease to Class I vs. Class II H–2 Differences," *J. Immunol.*, vol. 135 (1985) 3004–3010, published in USA.

Fidler, "The Relationship of Embolic Homogeneity, Number, Size and Viability to the Incidence of Experimental Metastases," *Eur. J. Cancer*, vol. 9 (1973) 223–227, published in Europe.

Kripke, "Latency, Histology, and Antigenicity of Tumors Induced by Ultraviolet Light in Three Inbred Mouse Strains," *Can. Res.*, vol. 37 (1977) 1395–1400, published in USA.

Ullrich et al., "Mechanisms in the Suppression of Tumor Rejection Produced in Mice by Repeated UV Irradiation," *J. Immunol.*, vol;. 133 (1984) 2786–2790, published in USA.

Ullrich et al., "Suppressor Lymphocytes Induced by Epicutaneous Sensitization of UV–Irradiated Mice Control Multiple Immunological Pathways," *Immunology*, vol. 58 (1986) 185–190, published in Europe.

Ullrich, "Suppression of the Immune Response to Allogeneic Histocompatibility Antigens by a Single Exposure to Ultraviolet Radiation," *Transplantation*, (1986) 42(3):287–291, published in USA.

Ullrich et al., "Specific Suppression of Allograft Rejection after Treatment of Recipient Mice with Ultraviolet Radiation and Allogeneic Spleen Cells," *Transplantation*, vol. 46 (1988) 115–119, published in USA.

Everett et al., "Penetration of Epidermis by Ultraviolet Rays", *Photochem. Photobiol.*, vol. 5 (1966) 533–542, published in USA.

Schwarz et al., "Inhibition of the Induction of Contact Hypersensitivity by a UV–Mediated Epidermal Cytokine," *J. Invest. Dermatol*, vol. 87 (1986) 289–291, published in USA.

Schwarz et al., "Uv–Irradiated Epidermal Cells Produce a Specific Inhibitor of Interleukin 1 Activity," *J. Immunol.*, vol. 138 (1987) 1457–1463, published in USA.

Liew et al., "Regulation of Delayed–Type Hypersensitivity. Vi. Antigen–Specific Suppressor T Cells and Suppressor Factor for Delayed–Type Hypersensitivity to Histocompatibility Antigens," *Transplantation*, vol. 33 (1982) 69–76, published in USA.

Swartz, "Suppression of Delayed–Type Hypersensitivity to Radiation [UV, 280–320 mm (UVB)]–Induced Tumor Cells with Serum Factors from UVB–Irradiated Mice," *J. Natl. Can. Inst.*, vol. 76 (1986) 1181–1184, published in USA.

Kupper et al., "Interleukin 1 Gene Expression in Cultured Human Keratinocytes Is Augmented by Ultraviolet Irradiation," *J. Clin. Invest.*, vol. 80 (1987) 430–436, published in USA.

Ansel et al., "The Expression and Modulation of IL–1 Alpha in Murine Keratinocytes," *J. Immunol.*, vol. 140 (1988) 2274–2278, published in USA.

Kripke, et al., "Studies on the Mechanism of Systemic Suppression of Contact Hypersensitivity by UVB Radiation. II. Differences in the Suppression of Delayed and Contact Hypersensitivity in Mice," *J. Invest. Dermatol.*, vol. 74 (1986) 543–549, published in USA.

Gensler et al., Item 1 from file 265, Dialog, printed in USA.
Berger et al., Item 3 from file 265, Dialog, printed in USA.
Noonan, Item 5 from file 265, Dialog, printed in USA.
Noonan, Item 6 from file 265, Dialog, printed in USA.
Elmets, Item 24 from file 265, Dialog, printed in USA.
Pierpaoli et al., European Patent Application Item 5 from file 351, Dialog, printed in USA.
Oluwole et al., Item 27/5/1 Embase, printed in USA.
Granstein et al., Item 27/5/6 Embase, printed in USA.
Morison et al., Item 27/5/13, Embase, printed in USA.
Morison et al., Item 34/5/10, Embase, printed in USA.
Dialog Search Report, includes the pertinent pages of a search, printed in USA.

Kupper et al., "Immunoregulation after Thermal Injury: Sequential Appearance of I–J$^+$, Ly–1 T Suppressor Inducer Cells and Ly–2 T Suppressor Effector Cells Following Thermal Trauma in Mice," *J. Immunol.*, vol. 135 (1984) 3047–3053, published in USA.

Kim, Tae–Yoon et al., "Immunosuppression by Factors Released from UV–Irradiated Epidermal Cells: Selective Effects on the Generation of Contact and Delayed Hypersensitivity after Exposure to UV–A or UV–B Radiation," *Biological Abstracts*, vol. 89 (1990) amd *J. Invest. Dermatol.* 94(1):26–32 (1990) (abstract 48803), published in USA.

Laemmli, U.K., "Cleavage of Structural Proteins During the Assembly of the Head of the Bacteriophage T4," *Nature*, 227:680 (1970), published in Europe.

Yoshikawa and Streilein, "Tumor Necrosis Factor–Alpha and Ultraviolet B Light Have Similar Effects on Contact Hypersensitivity in Mice," *Regional Immunology*, 3(3)9–144, 1990/1991, published in USA.

Köck et al., "Human Keratinocytes are a Source for Tumor Necrosis Factor α: Evidence for Synthesis and Release upon Stimulation with Endotoxin or Ultraviolet Light," *The Journal of Experimental Medicine*, 172:1609–1614, 1990, published in USA.

Fiorentino et al., "IL–10 Acts on the Antigen–Presenting Cell to Inhibit Cytokine Production by Th1 Cells," *The Journal of Immunology*, 146(10)3444–3451, 1991, published in USA.

Luger and Schwarz, "Epidermal Cell–Derived Cytokines," in *Skin Immune System*, Jan D. Bos, Ed., CRC Press, Inc., Boca Raton, Florida, pp. 257–291, 1990, published in USA.

Jeevan et al., "Supernatants from Ultraviolet–Irradiated Keratinocytes Decrease the Resistance and Delayed–Type Hypersensitivity Response to *Mycobacterium bovis* Bacillus Calmette–Guerin in Mice and Impair the Phagocytic Ability of Macrophages," *Photodermatol Photoimmunol Photomed*, 9:255–263, 1992, published in Europe.

Urbach, Frederick, "Welcome and Introduction: Evidence and Epidemiology of Ultraviolet–Induced Cancers in Man," *National Cancer Institute Monograph No. 50*, pp. 5–10, 1977, published in USA.

Ullrich, Stephen E., "The Role of Keratinocyte–Derived Suppressive Cytokines in the Systemic Immunosuppression Induced by Ultraviolet B Radiation," *Trends in Photochemistry & Photobiology*, 2:137–154, 1991, place of publication unknown.

Rivas and Ullrich, "Systemic Suppression of Delayed–Type Hypersensitivity by Supernatants from UV–Irradiated Keratinocytes: An Essential Role for Keratinocyte–Derived IL–10," *The Journal of Immunology*, 149(12):3865–3871, 1992, published in USA.

Rivas and Ullrich, "Keratinocyte–Derived IL–10," *Journal of Investigative Dermatology*, Abstract No. 160, May, 1992, published in USA.

Akhurst et al., "Localized Production of TGF–β mRNA in Tumour Promoter–Stimulated Mouse Epidermis," *Nature*, 331:363–365, 1988, published in Europe.

Ansel et al., "Cytokine Modulation of Keratinocyte Cytokines," *J. Invest. Dermatol.*, 94:101S–107S, 1990, published in USA.

Aubin et al., "Activation of Keratinocytes with Psoralen plus UVA Radiation Induces the Release of Soluble Factors that Suppress Delayed and Contact Hypersensitivity," *J. Invest. Dermatol.*, 97:995–1000, 1991, published in USA.

Cherwinski et al., "Two Types of Mouse Helper T Cell Clone. III. Further Differences in Lymphokine Synthesis between Th1 and Th2 Clones Revealed by RNA Hybridization, Functionally Monospecific Bioassays, and Monoclonal Antibodies," *J. Exp. Med.*, 166:1229–1244, 1987, published in USA.

Chung et al., "Involvement of Prostaglandins in the Immune Alterations Caused by the Exposure of Mice to Ultraviolet Radiation," *The Journal of Immunology*, 137(8):2478–2484, 1986, published in USA.

Fiorentino et al., "Two Types of Mouse T Helper Cells. IV. Th2 Clones Secrete a Factor that Inhibits Cytokine Production by Th1 Clones," *J. Exp. Med.*, 170:2081–2095, published in USA.

Gazzinelli et al., "IL–10 Inhibits Parasite Killing and Nitrogen Oxide Production by IFN–γ–Activated Macrophages," *The Journal of Immunology*, 148(6):1792–1796, 1992, published in USA.

Gottlieb et al., "Synthetic Peptide Corresponding to a Conserved Domain of the Retroviral Protein p15E Blocks IL–1–Mediated Signal Transduction," *The Journal of Immunology*, 142(12):4321–4328, 1989, published in USA.

Halliday and Muller, "Sensitization through Carcinogen–Induced Langerhans Cell–Deficient Skin Activates Specific Long–Lived Suppression Cells for Both Cellular and Humoral Immunity," *Cellular Immunology*, 109:206–221, 1987, published in USA.

Harriott–Smith and Halliday, "Suppression of Contact Hypersensitivity by Short–Term Ultraviolet Irradiation: I. Immunosuppression by Serum from Irradiated Mice," *Clin. Exp. Immunol.*, 71:144–148, 1988, published in Europe.

Kodari et al., "Induction of Suppressor T Cells and Inhibition of Contact Hypersensitivity in Mice by 12–O–Tetradecanoylphorbol–13–Acetate and Its Analogs," *J. Invest. Dermatol.*, 96:864–870, 1991, published in USA.

Kripke, "Antigenicity of Murine Skin Tumors Induced by Ultraviolet Light," *Journal of the National Cancer Institute*, 53(5):1333–1336, 1974, published in USA.

Krutmann et al., "Epidermal Cell–Contra–Interleukin 1 Inhibits Human Accessory Cell Function by Specifically Blocking Interleukin 1 Activity," *Photochemistry and Photobiology*, 52(4):783–788, 1990, published in Europe.

Mizutani et al., "Human Keratinocytes Produce but Do Not Process Pro–Interleukin–1 (IL–1) Beta: Different Strategies of IL–1 Production and Processing in Monocytes and Keratinocytes," *J. Clin. Invest.*, 87:1066–1071, 1991, published in USA.

Moore et al., "Homology of Cytokine Synthesis Inhibitory Factor (IL–10) to the Epstein–Barr Virus Gene BCRFI," *Science*, 248:1230–1234, 1990, published in USA.

Mosmann, "Regulation of Immune Responses by T Cells with Different Cytokine Secretion Phenotypes: Role of a New Cytokine, Cytokine Synthesis Inhibitory Factor (IL10)," *Int. Arch. Allergy Appl. Immunol.*, 94:110–115, 1991, published in Europe.

Mosmann et al., "Isolation of Monoclonal Antibodies Specific for IL–4, IL–5, IL–6, and a New Th2–Specific Cytokine (IL–10), Cytokine Synthesis Inhibitory Factor, by Using a Solid Phase Radioimmunoadsorbent Assay," *The Journal of Immunology*, 145(9):2938–2945, 1990, published in USA.

Norbury et al., "In Vitro Reactivity of Macrophages and Lymphocytes from Ultraviolet–Irradiated Mice," *J. Natl. Cancer Inst.*, 59(4):1231–1235, 1977, published in USA.

Parish, "The Relationship Between Humoral and Cell–Mediated Immunity," *Transplant. Rev.*, 13:35–66, 1972, published in Europe.

Spellman et al., "Modification of Immunological Potential by Ultraviolet Radiation," *Transplantation*, 24(2):112–119, 1977, published in USA.

Ullrich et al., "Suppression of the Immune Response to Alloantigen by Factors Released from Ultraviolet–Irradiated Keratinocytes," *The Journal of Immunology*, 145(2):489–498, 1990, published in USA.

Rivas et al. J. Immunology 149(12):3865–71 Dec. 15, 1992.

Mosmann et al. J. Immunology 145(9):2938–45 Nov. 1990.

Ullrich et al. J. Immunology 145(2):489–98 Jul. 1990.

Ullrich et al. Transplantation 46(1):115–19 Jul. 1988.

Kim et al. J. Invest. Dermatol. 94(1):26–32 Jan. 1990.

UV-INDUCED FACTOR FOR IMMUNOSUPPRESSION

This application is a continuation of application Ser. No. 07/987,760, filed Dec. 8, 1992, now abandoned, which is a continuation-in-part application of Ser. No. 07/768,232 filed Oct. 10, 1991, now abandoned, which is a continuation of PCT/US90/01402 filed Mar. 14, 1990. The PCT application is a continuation-in-part of U.S. Ser. No. 07/323,615 filed Mar. 14, 1989 now abandoned. These applications are incorporated by reference herein.

The U.S. Government has rights in the present invention due to grant support from RO1-AR 40824, CA-09598 and CA-16672.

BACKGROUND OF THE INVENTION

Two kinds of effector mechanisms mediate immune responses. Some immune responses are mediated by specific molecules, called antibodies, that are carried in the blood and lymph. The synthesis of antibodies occurs in a subset of lymphocytes called B lymphocytes or B cells. Antibody-mediated immunity is called humoral immunity. Other immune responses are mediated by cells. All the leukocytes (white cells) of the blood participate in cell-mediated immunity (CMI). However, the specificity of the response depends upon a subset of lymphocytes called T lymphocytes or T Cells. Most immune responses involve the activity and interplay of both the humoral and the cell-mediated branches of the immune system.

Ultraviolet radiation is a major environmental carcinogen and the primary cause of non-melanoma skin cancer worldwide (Urbach, 1978). In addition to being a carcinogen, UV radiation is also immunosuppressive, and studies using mice have demonstrated an intimate link between the immunosuppressive effects of UV radiation and the development of skin cancer (Kripke, 1974). The suppression induced by UV radiation is unique. Despite the limited ability of UV to penetrate tissue (Evertt et al., 1966), the suppression seen following exposure to UV radiation is systemic. For example, after a single exposure to UV radiation, mice are unable to generate a delayed-type hypersensitivity reaction to antigens injected subcutaneously at a distant non-irradiated site (Ullrich et al., 1986a; Ullrich, 1986b; Molendijk et al., 1987). The suppression is specific for the injected antigen, and associated with the appearance of splenic antigen-specific suppressor T lymphocytes (Ullrich et al., 1988). Although it is not entirely clear how UV-irradiation of the skin can result in the induction of systemic immunosuppression, most of the evidence to date supports the concept that UV-induced soluble suppressive factors are involved. Indeed a wide variety of soluble factors have been implicated in the induction of systemic suppression following UV exposure, including cis-urocanic acid (De Fabo et al., 1983), contra-IL-1 (Schwarz et al., 1987), IL-1, (Robertson et al., 1987) prostaglandins (Chung, H. T. et al., 1986), serum factors (Swartz, R. P, 1984; Harriott-Smith, T. G. et al., 1988), and factors isolated from UV-irradiated keratinocytes (Schwarz, T. A. et al., 1986; Kim, T. Y. et al., 1990; Ullrich, S. E. et al., 1990).

Furthermore, the suppression observed following UV exposure is unique in that the immunosuppressive effect is highly selective. Although cell mediated immune reactions such as the rejection of UV-induced tumor cells, delayed-type hypersensitivity (DTH) and contact hypersensitivity (CHS) are suppressed in UV-irradiated mice, most other immune reactions, especially antibody production, are normal (Spellman, C. W. et al., 1977; Norbury, K. C. et al., 1977). Similarly, injecting supernatants from UV-irradiated keratinocyte cultures only suppresses the induction of cellular immune reactions; antibody production is normal in factor-injected mice (Kim, T. Y. et al., 1990).

The present inventors and others have provided evidence for the role of keratinocyte-derived cytokines in the induction of suppression following UV exposure. (Kim, T. Y. et al., 1990; Ullrich, S. E. et al., 1990; Luger, T. A. et al., 1989; Aubin, F. et al., 1991). The immunosuppression seen following total-body UV exposure and the suppression observed after injecting supernatants from UV-irradiated keratinocytes are selective in nature. Although cellular immune reactions such as DTH are suppressed, antibody formation is normal. (Kim, T. Y. et al., 1990; Spellman, C. W. et al., 1977; Norbury, K. C. et al., 1977). Two of the major immunologic defects associated with UV-induced systemic suppression are the suppression of delayed-in-time hypersensitivity reactions and depressed antigen-presenting cell capability (Kripke, M. L. 1984).

Another prominent suppressive cytokine implicated in the suppression of CHS following UV exposure in vivo is TNF-$\alpha$. (Yoshikawa, T. et al., 1990). Although others have reported that keratinocytes release TNF-$\alpha$ after exposure to UV radiation, (Kock, A. et al., 1990) the present inventors were unable by Western analysis to find TNF-$\alpha$ in the keratinocyte supernatant of the present invention nor did treatment of the supernatant with anti-TNF-$\alpha$ antibody neutralize the suppressive activity. However, although these observations demonstrate that there is no TNF-$\alpha$ in this suppressive supernatant they do not rule out a role for TNF-$\alpha$ in the induction of suppression following UV exposure. Ansel et al. (1990), found that a number of agents are capable of activating keratinocytes to release cytokines, including the cytokines themselves. For example, IL-1 MRNA expression was up-regulated by incubating the keratinocytes in IL-1, TNF-$\alpha$, or granulocyte-macrophage colony stimulating factor (GM-CSF). Similarly, GM-CSF mRNA expression was up-regulated after incubation with IL-2, TNF-$\alpha$, or GM-CSF. It is possible that a similar situation occurs with keratinocyte-derived suppressor cytokines.

The induction of suppression by keratinocyte-derived suppressive cytokines and the selective nature of the immunosuppression generated following the injection of supernatants from UV-irradiated keratinocytes led the present inventors to focus attention on a suppressive cytokine, IL-10. Studies by Mosmann and colleagues demonstrated that CD4+T lymphocytes can be divided into two subclasses based on the pattern of cytokines released after antigenic stimulation. Th1 cells secrete IL-2, IFN-$\gamma$ and lymphotoxin, whereas Th2 cells produce IL-4, IL-5, IL-6 and IL-10 following antigenic stimulation. For the most part, Th1 cells, because of the cytokines they release, are more active in providing help for cellular immune reactions, whereas Th2 cells are much more efficient at providing help for humoral immune reactions (Florentino, D. F. et al., 1989). Moreover, there appears to be a cross-regulation between these two subsets of helper cells during an immune response. IFN-$\gamma$ production by Th1 cells prevents the proliferation of Th2 cells, thus limiting humoral immune reactions, and IL-10 secreted by Th2 cells interferes with cytokine production by Th1 cells, thus limiting cellular immune reactions. This cross-regulation by Th1 and Th2 cells may help to explain the observation that antibody production and DTH are often mutually exclusive (Parish, C. R., 1972). IL-10 has been implicated in the suppression of DTH and inhibits antigen-presenting cell activity. (Florentino, D. F. et al., 1991; Mosmann, T. R., 1991).

Other keratinocyte and epidermal-derived soluble suppressive factors have also been implicated in the induction of immunosuppression following UV exposure (Ullrich, S. E., 1991). Two of the hallmarks of the systemic suppression induced by UV radiation are the suppression of DTH and CHS and a systemic depression of antigen-presenting cell capability. Of the various suppressive factors that have been implicated in the induction of systemic suppression by UV radiation, only a few have been shown to inhibit both delayed-in-time-hypersensitivity reactions and antigen-presenting cell function. Schwarz and colleagues have described factors from UV-irradiated keratinocytes that suppress CHS (contra-CHS) and IL-1-induced thymocyte activation (contra-IL-1). (Schwarz et al., 1987; Schwarz, T. A. et al., 1986). Contra-IL-1 has been found in the serum of UV-irradiated human volunteers and is associated with depressed antigen-presenting cell capability. (Krutmann, J. et al., 1990). UV exposure also promotes the conversion of trans-urocanic acid to the cis-isomer, and cis-urocanic acid suppresses both DTH reactions and systemic antigen-presenting cell activity. (Ross, J. A. et al., 1988; Noonan, F. P. et al., 1988). The present invention demonstrates that keratinocyte-derived IL-10 suppresses the induction of DTH. The present inventors have shown previously that splenic adherent cells isolated from mice injected with supernatants from UV-irradiated keratinocytes were ineffective at presenting haptens for a DTH reaction. (Ullrich, S. E., 1991). Furthermore, injecting supernatants from UV-irradiated keratinocytes into mice suppresses host resistance to *Mycobacterium bovis* BCG by suppressing DTH and interfering with bacterial clearance. (Jeevan, A. et al., 1992). This suppression of antigen-presenting cell activity and inhibition of microbial killing is consistent with the reported functions of IL-10. (Florentino, D. F. et al., 1991; Gazzinelli, R. T. et al., 1992).

The release of IL-10 by UV-irradiated keratinocytes may also explain the selective suppression (i.e., inhibition of cell-mediated immune reactions but not of antibody production) observed following UV exposure or the injection of supernatants from UV-irradiated keratinocytes. Therefore, the purpose of the present study was to determine whether IL-10 is released by keratinocytes following UV exposure. Furthermore, the present inventors also examined the ability of neutralizing monoclonal antibodies against IL-10 to inhibit the induction of systemic suppression observed following the injection of supernatants from UV-irradiated keratinocytes into mice or following total-body UV exposure.

The study of the systemic suppression of the immune system by UV-radiation is important for a number of reasons. First, an association between immunosuppression and the development of primary skin cancers in mice has been demonstrated [Fischer, 1982]. Insight into the mechanism by which UV-radiation suppresses the immune response may be helpful in providing new approaches for the treatment and/or prevention of skin cancer. Second, the systemic immunologic alterations caused by UV-radiation, especially the suppression of DTH, may be a predisposing factor for an increased incidence of infectious diseases. This coupled with a decrease in the atmospheric ozone layer suggests that UV-induced immunosuppression may adversely affect the health of wide segments of the population. Finally, the immunosuppression induced by UV-radiation may have therapeutic applications, e.g., in the suppression of allograft rejection.

The present inventor has demonstrated that at least two factors are involved in UV induced CHS and DTH suppression, each being released by cells after irradiation with different wavelengths of UV-radiation. The present inventor has determined that supernatant from epidermal cells exposed to long-wave UV radiation, UVA, (320–400 nm) would suppress CHS but not DTH. On the other hand, supernatants from short-wave UV-radiation, UVB, (280–320 nm) would suppress DTH but not CHS. This result shows that two different immunosuppressive factors are released by UV-irradiated cells. The first immunosuppressive is released on exposure to UVB and suppresses DTH and the second is released on exposure to UVA and suppresses CHS. Therefore, by using a pre-determined wavelength of ultraviolet radiation (UVR), e.g., UVA or UVB, the immune response of a mammal can be selectively suppressed.

Typically, to overcome the immunological rejection of transplanted tissue (allografts), immunosuppressive drugs are used. One serious side effect of many of these agents, however, is the pan-immunosuppression that is produced. In addition to the suppression of allograft rejection, all other immune responses, such as those involved in the protection of the host from viral and bacterial pathogens, are also suppressed. As a result the immunosuppressed patient is susceptible to a variety of opportunistic infections. Accordingly, a method of suppressing only the immune response to the allografted tissue while leaving other immunological functions intact would be highly advantageous.

It has been reported that direct UV-irradiation (UVR) of the allograft can result in prolonged survival (Lau et al., 1983; Lau et al., 1984), of the allograft. The mechanism suggested there is an alteration of the antigenic composition of the grafted tissue by the UVR, thus rendering the allograft nonantigenic. In the present invention, however, an alternative approach of rendering the recipient tolerant to the allograft is taken.

SUMMARY OF THE INVENTION

In the present invention a specific immunosuppressive factor reactive with an antibody directed toward IL-10 is produced in vivo, by a subject mammal, or in vitro, by an epidermal cell, when either is irradiated with a sufficient amount of a pre-determined wavelength of UVR. This immunosuppressive factor, combined with subsequent antigenic sensitization of an animal, induces an immunosuppression which is specific for the antigenic determinants used to sensitize the animal. Thus, pan-immunosuppression is avoided. In this regard the use of a pre-determined wavelength of UVR to induce selective immunosuppression may have a marked advantage over the use of immunosuppressive drugs such as azathioprine or corticosteroids. Accordingly, the method of administering a sufficient amount of an immunosuppressive factor to selectively suppress an immune response in a mammal to a particular antigen would have advantageous applications in the suppression of graft rejection after organ transplantation. For example, it would be advantageous to use the methods of the present invention to selectively suppress DTH and graft rejection while leaving the immune system of a patient otherwise uncompromised.

One aspect of the present invention is a method for selectively suppressing an immune response in a mammal to a particular antigen following the administration of an immunosuppressive factor and subsequent sensitization of the mammal to the particular antigen. The method may include multiple steps. One step is irradiating an epidermal cell culture with a sufficient amount of UV-radiation having a pre-determined wavelength to create an immunosuppressive factor. It has been determined that mammalian epidermal cells irradiated with UVB radiation (pre-determined wavelength of UVB-radiation being 280 to 320 nm) will produce an immunosuppressive factor which selectively suppresses the DTH response in mammals.

Another step in the inventive method involves extracting the immunosuppressive factor from the UV-irradiated cells. A further step in the inventive method involves administering an effective amount of the immunosuppressive factor to the mammal. Thereafter, the mammal is sensitized to the particular antigen for which immunotolerance is preferred.

Yet another aspect of the present invention is the process for producing an immunosuppressive factor and the immunological suppressive factor itself. This aspect of the invention preferably produces an immunosuppressive factor which may be subsequently administered to a subject animal to result in a selective suppression of a specific immune response to a particular antigen. The inventive process includes the steps of radiating a plurality of epidermal cells in vitro with a sufficient amount of a pre-determined wavelength of UV-radiation to produce UV-irradiated cells producing an immunosuppressive factor. It has been determined that mammalian cells irradiated in vitro with a sufficient amount of UVB (pre-determined wavelength being 280 to 320 nm) will produce an immunosuppressive factor reactive with an antibody directed toward IL-10 which selectively suppresses the DTH response in mammals when administered in a sufficient amount.

A single exposure to ultraviolet radiation induces a systemic suppression of the immune response to allogeneic histocompatibility antigens. The suppression is associated with the appearance of splenic alloantigen-specific suppressor T cells. How exposing the skin to UV radiation results in the induction of splenic suppressor T cells is not entirely clear. The data described herein suggest the involvement of a UV-induced keratinocyte-derived suppressive factor reactive with an antibody directed toward IL-10. The keratinocyte line, Pam 212 was exposed to 200 J/$m^2$ of UVB radiation from a single FS-40 sunlamp and cultured overnight in serum-free medium. Injecting mice with culture supernatants from UV-irradiated keratinocytes suppressed the induction of delayed type hypersensitivity to alloantigen. Injecting supernatants from non-irradiated Pam 212 cells had no suppressive effect. Antigen-specific T suppressor cells were found in the spleens of the mice injected with the suppressive supernatants. Cycloheximide treatment of keratinocytes and trypsinization of the supernatants from the UV-irradiated keratinocytes resulted in a loss of suppressive activity suggesting the involvement of a protein. The suppressive material bound to a Concanavalin A-agarose lectin-affinity column and was eluted with α-D-mannopyranoside, indicating that the suppressive material is a glycoprotein. These data support the hypothesis that soluble factors released from UV-irradiated keratinocytes are responsible for the induction of systemic suppression following exposure to UV radiation, by demonstrating that the injection of these factors induces antigen-specific suppressor T cells.

A unique feature of the immunosuppression induced by either total-body UV-exposure or injecting the suppressive cytokine from UV-irradiated keratinocytes is the selectivity of suppression. Although cellular immune reactions such as delayed-type hypersensitivity are suppressed, antibody production is unaffected. In a preferred embodiment of the present invention, the suppressive cytokine is an immunosuppressive factor reactive with an antibody directed toward IL-10. Keratinocyte monolayers were exposed to UV radiation and at specific times after exposure mRNA was isolated or the culture supernatant from the cells was collected. IL-10 mRNA expression was enhanced in UV-irradiated keratinocytes. The secretion of an immunosuppressive factor reactive with an antibody directed toward IL-10 by the irradiated keratinocytes was determined by Western blot analysis. A band reactive with anti-IL-10 monoclonal antibody was found in supernatants from the UV-irradiated but not the mock-irradiated cells. IL-10 biological activity was determined by the ability of the supernatants from the UV-irradiated keratinocytes to suppress interferon-γ production by antigen-activated T helper 1 cell clones. Monoclonal anti-IL-10 antibody neutralized the ability of supernatants from UV-irradiated keratinocytes to suppress the induction of delayed-type hypersensitivity in vivo. Furthermore, injecting UV-irradiated mice with antibodies against IL-10 inhibited in vivo immunosuppression. These data indicate that activated keratinocytes are capable of secreting an immunosuppressive factor reactive with an antibody directed toward IL-10 and indicate that the release of said immunosuppressive factor by UV-irradiated keratinocytes plays an essential role in the induction of systemic immunosuppression following total-body UV exposure.

In a preferred embodiment of the present invention, keratinocytes, after UV exposure, release an immunosuppressive factor reactive with an antibody directed toward IL-10 and the release of said immunosuppressive factor is at least partially responsible for the induction of systemic immuno-suppression. This aspect of the present invention results from the following discoveries by the present inventors: i) IL-10 mRNA expression is up-regulated in UV-irradiated keratinocytes, ii) a protein released by UV-irradiated keratinocytes that was reactive with monoclonal anti-IL-10 antibody on an immunoblot was identified, iii) supernatants from UV-irradiated keratinocytes had IL-10-like biological activity, as measured by their ability to suppress IFN-γ production by antigen-activated Th1 cells, iv) treating the supernatants from UV-irradiated keratinocytes with neutralizing monoclonal anti-IL-10 antibody totally removed all immunosuppressive activity, v) injecting UV-irradiated mice with anti-IL-10 monoclonal antibody partially blocked the suppressive effects of UV exposure. Thus, these data demonstrate that UV-irradiated keratinocytes secrete a factor with IL-10 biological activity and that said factor is responsible for the suppression of DTH found after injecting supernatants from UV-irradiated keratinocytes into mice. Moreover, these findings suggest that the release of said immunosuppressive factor by UV irradiated keratinocytes in vivo is at least partially responsible for the induction of immuno-suppression found following total-body UV exposure.

An aspect of the present invention is an immunosuppressive factor produced by UVB irradiated epidermal cells which selectively suppresses DTH in a mammal, said factor being reactive with an antibody directed toward IL-10. Another aspect of the present invention is a preparation comprising said factor usable to prevent host rejection of a graft in a mammal. Said preparation is produced by epidermal cells irradiated with from about 10 J/$m^2$ to about 200 J/$m^2$ of UVB radiation.

A further aspect of the present invention is a glycoprotein reactive with an antibody directed toward IL-10 and which is capable of suppressing an immune response of a mammal. The glycoprotein is produced by epidermal cells subjected to UV radiation, in particular, UVB irradiation. The glycoprotein is bound by a concanavalin A-agarose affinity matrix and is eluted from said matrix by alpha D-mannopyranoside. The immune response suppressed is delayed-type hypersensitivity and the epidermal cells include keratinocytes and Pam 212 cells.

The present invention includes a method of selectively suppressing immune response of a mammal to a particular antigen, comprising; (a) irradiating an epidermal cell culture capable of producing an immunosuppressive factor reactive with an antibody directed toward IL-10 with an amount of UV-radiation having a pre-determined wavelength, the amount being sufficient to induce the cell culture to produce an immunosuppressive factor; (b) extracting the immunosuppressive factor from said UV-irradiated cell culture; (c) administering an effective amount of the immunosuppressive factor to a mammal; and (d) sensitizing the mammal to a particular antigen.

In this particular method the epidermal cell culture is a single somatic cell type, the irradiating step involves UVB-radiation having a pre-determined wavelength of from about 280 nm to about 320 nm, and the immunosuppressive factor selectively suppresses DTH response in a mammal. Also claimed is the same method wherein immediately after step (a), cells from the irradiated cell culture are suspended in a nutritive media and, further, wherein step (b) comprises separating cells from the nutritive media, the nutritive media now including the immunosuppressive factor. In this method the amount of UV-radiation may be from about 10 $J/m^2$ to about 200 $J/m^2$. Included in this method is wherein step (d) comprises the parenteral administration of the particular antigen, the parenteral administration is intravascular, intraperitoneal, subcutaneous or intramuscular. A preferred embodiment is wherein step (d) comprises the subcutaneous administration of the particular antigen. Included in this method is wherein step (c) comprises parenteral administration of the immunosuppressive factor to the mammal wherein the parenteral administration is intravascular, intraperitoneal, subcutaneous or intramuscular and in particular, wherein step (c) involves intravenous administration.

A preferred embodiment of the present invention is where the immune response suppressed is the delayed type hypersensitivity (DTH) response in a mammal.

Another aspect of the present invention is a method for reducing incidence of Graft versus Host Disease (GVHD) in a mammal, comprising: (a) administering to a prospective bone marrow cell donor an effective amount of an immunosuppressive factor reactive with an antibody directed toward IL-10; (b) sensitizing the prospective donor thereafter to antigens of a prospective bone marrow cell recipient; and (c) transplanting bone marrow cells from the prospective donor to the prospective bone marrow cell recipient.

Included in this method is where the administering step comprises parenteral administration of the immunosuppressive factor to the mammal where the parenteral administration is intravascular, intraperitoneal, subcutaneous, or intramuscular. The preferred administrating step involves intravenous administration. Included in this method is where the sensitizing step involves parenteral administration of the antigen, wherein the parenteral administration is intravascular, intraperitoneal, intramuscular or subcutaneous and, in particular, the sensitizing step is subcutaneous administration. Also included in this method is where the sensitizing step is epicutaneous application of a sample bearing antigens of the prospective bone marrow recipient.

A further preferred embodiment of the present invention is a process for producing an immunosuppressive factor reactive with an antibody directed toward IL-10 and which selectively suppresses immune response in a mammal, comprising; irradiating a plurality of epidermal cells capable of producing an immunosuppressive factor with an amount of UV-radiation having a pre-determined wavelength, the amount being sufficient to result in UV-irradiated cells producing an immunosuppressive factor; and extracting the immunosuppressive factor. In this process the epidermal cells are irradiated in vitro and the amount of UV-radiation is from about 10 $J/m^2$ to about 200 $J/m^2$. In particular, the UV-radiation is UVB radiation, and the immune response suppressed is the delayed type hypersensitivity response.

A further aspect of the present invention is a method of selectively suppressing immune response in a mammal, in particular, DTH, to a particular antigen, comprising: (a) administering an effective amount of IL-10 to a mammal; and (b) sensitizing the mammal to a particular antigen.

The sensitizing step comprises parenteral administration of the particular antigen where the parenteral administration is intravascular, intraperitoneal, intramuscular or subcutaneous, and in particular, the antigen is administered subcutaneously. The administering step comprises parenteral administration where parenteral administration is intravascular, intraperitoneal, subcutaneous or intramuscular and, in particular, is intravenous.

A further aspect of the present invention is a method for reducing incidence of GVHD in a mammal comprising administering to a prospective bone marrow cell donor an effective amount of IL-10; sensitizing the prospective donor thereafter to antigens of a prospective bone marrow cell recipient; and transplanting bone marrow cells from the prospective donor to the prospective bone marrow cell recipient. The administering step comprises parenteral administration of IL-10 where the parenteral administration is intravascular, intraperitoneal, subcutaneous or intramuscular, in particular, the preferred administration is intravenous. The sensitizing step involves parenteral administration of the antigen wherein the parenteral administration is intravascular, intraperitoneal, intramuscular or subcutaneous, in particular, subcutaneous administration. The sensitizing step may be epicutaneous application of a sample bearing antigens of the prospective bone marrow recipient. In a preferred embodiment of the present invention, antigens may be alloantigens.

Abbreviations used:

ATBM—allogenic T-cell depleted bone marrow

CHS—contact hypersensitivity

DTH—delayed-type hypersensitivity

GM-CSF—granulocyte-macrophage colony stimulating factor

NR-SN—supernatant from mock-irradiated keratinocytes

TGF-β—transforming growth factor-beta

UVA—ultraviolet radiation of wavelength 320 nm to 400 nm predominating

UVB—ultraviolet radiation of wavelength 280 nm to 320 nm predominating

UVR—ultraviolet radiation

UV-SN—supernatant from UV-irradiated keratinocytes

DETAILED DESCRIPTION OF THE PREFERRED EMBODIMENTS

Figure 1A:
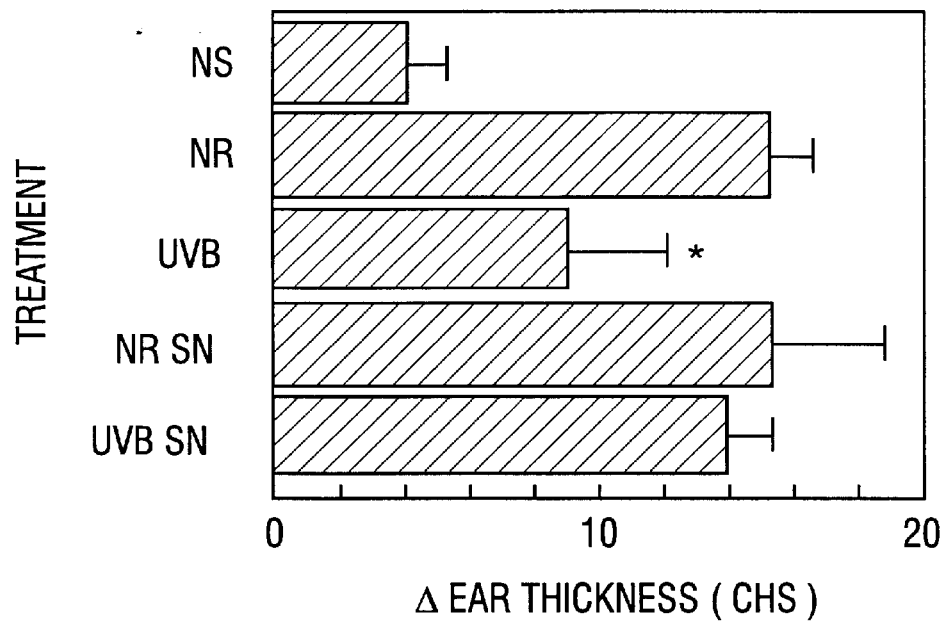
FIG. 1A and FIG. 1B shows the effect of the supernatants from UV-irradiated primary epidermal cell cultures on the induction of CHS(A) or DTH(B). Mice were injected with supernatants from the UVB-irradiated (UVB-SN) or control (NRSN) epidermal cell cultures or exposed to 40 kJ/m$^2$ of UVB radiation (UVB). In panel A, C3H mice were sensitized with TNCB, in panel B, C3H mice were sensitized with BALB/c spleen cells. The asterisk indicates a significant difference (P<0.001) from the response observed in the positive control (NR). The background response was measured in mice that were challenged but not sensitized with the antigen (NS). There were 5 mice per group: units=cm× $10^{-3}$.

The selective suppression of a specific immune response to a particular alloantigen by a pre-determined wavelength of ultraviolet radiation is illustrated by experiments in which mice are irradiated with a sufficient dose of UV-radiation and subsequently sensitized to particular alloantigen. According to one preferred embodiment, the DTH response to the particular alloantigen is depressed by whole body UVB-irradiation (pre-determined wavelength 280 nm–320 nm) and subsequent sensitization with the particular alloantigen. Whole body irradiation is defined as the process of irradiating the epidermis of the subject animal.

The mechanism of whole body UV-induced immunosuppression is the release of immunosuppressive factors by UV-irradiated cells.

The present inventor has demonstrated that these immunosuppressive factors are contained in the supernatants from epidermal cell cultures exposed to pre-determined wavelengths of UV-radiation. Moreover, the immunosuppressive factors produced in vitro are potent, suppressing the induction of CHS or DTH, depending on the wavelength of UV-radiation used. In addition, it should be noted that the suppression induced by these immunosuppressive factors remains selective in nature. Thus, cells in vitro irradiated with selected or pre-determined wavelengths of UV-radiation, e.g., UVA (320 nm to 400 nm), or UVB (280 nm to 320 nm), produce immunosuppressive factors which, when administered to a subject individual, will selectively suppress an immune response in the subject individual. Accordingly, the immune response of the subject individual is not totally incapacitated, leaving much of the immune response uncompromised to protect against opportunist pathogens.

One aspect of the present invention is directed to the suppression of a specific immune response to a particular alloantigen in a mammal by administering immunosuppressive factors obtained from UV-irradiated cells to the subject mammal, thereafter sensitized to the particular alloantigen. Another aspect of the present invention is directed to the suppression of a specific immune response to a particular alloantigen by whole body UV-irradiation and subsequent sensitization to the particular alloantigen. The inventor has demonstrated that immunosuppressive factors released from either UVB-irradiated Pam 212 cells or primary epidermal cell cultures can mimic the effects of whole-body UVB-irradiation and suppress DTH. On the other hand, these same immunosuppressive factors were unable to suppress CHS. However, keratinocytes irradiated with UVA-radiation were able to generate a immunosuppressive factor that suppressed CHS. Moreover, the injection of the immunosuppressive factors from the UVA-irradiated keratinocytes did not suppress DTH. Thus, the present inventor has shown that the immunosuppressive factors released from UV-irradiated epidermal cells are responsible for the induction of selective systemic immunosuppression by UV radiation. The data presented herein indicates that aspects of the selective systemic immunosuppression by UV-radiation are controlled by two immunosuppressive factors, each one released after irradiation of cells with different wavelengths of UV light.

One aspect of the invention is directed to a method for selectively suppressing an immune response of a mammal to a particular alloantigen. This inventive method includes the steps of: (a) administering to a mammal an effective amount of UV-radiation having a pre-determined wavelength; and (b) sensitizing the animal thereafter to the particular alloantigen.

The first step in this inventive method is administering an effective amount of UV-radiation having a pre-determined wavelength to a mammal. In a preferred embodiment, the UV-radiation is UVB-radiation having a pre-determined wavelength of 280 nm–320 nm. The UV-radiation is preferably administered to the mammal by irradiating the epidermis of the mammal, e.g., whole body irradiation. The effective amount of the UV-radiation is preferably from about 10 to about 100 $kJ/m^2$, and most preferably, from about 30 to about 60 $kJ/m^2$.

The next step of the inventive method is sensitizing the mammal thereafter to the particular alloantigen. The mammal is preferably sensitized by the injection of the particular alloantigen. The injection may be intravenous, intraperitoneal, intramuscular, subcutaneous or intrathecal. According to one embodiment of the invention, the mammal is sensitized by the intramuscular injection of the particular alloantigen. According to a preferred embodiment of the invention, the mammal is sensitized by the subcutaneous injection of the particular alloantigen. According to another preferred embodiment, the mammal is sensitized by the epicutaneous application of the alloantigen.

It is demonstrated herein that sensitized UV-irradiated animals develop a specific immunotolerance to the sensitizing alloantigen. For example, mice irradiated with UVB-radiation have suppressed DTH responses to the particular sensitizing alloantigen and a suppressed CHS response to the particular sensitizing alloantigen. Accordingly, the DTH or CHS response in a mammal may be selectively suppressed to a particular alloantigen depending on the wavelength of the UV radiation administered to the mammal.

Another aspect of the present invention is directed to methods of making and using immunosuppressive factors which induce a specific immunotolerance to a particular alloantigen in a subject mammal. The inventive method includes the steps of: (a) irradiating a plurality of mammalian cells in vitro, with an effective amount of UV-radiation having a pre-determined wavelength to create UV-irradiated cells producing immunosuppressive factors; (b) extracting the immunosuppressive factors from the UV-irradiated cells; (c) administering an effective amount of the immunosuppressive factors to a mammal; and (d) sensitizing the mammal thereafter to the particular alloantigen.

The first step of the inventive method is irradiating a plurality of mammalian cells in vitro with an effective amount UV-radiation having a pre-determined wavelength to create UV-irradiated cells producing immunosuppressive factors. Preferred cells include epidermal cells and may be those of the subject to be treated. Preferably, the UV-radiation is UVB-radiation.

It is demonstrated herein that mammalian cells irradiated in vitro with an effective amount of UVA-radiation produce immunosuppressive factors which, when administered in an effective amount to a subject mammal which is subsequently sensitized to a particular alloantigen, selectively suppress the CHS response in that mammal to that particular alloantigen. On the other hand, it has been demonstrated that mammalian cells irradiated in vitro with an effective amount of UVB-radiation produce immunosuppressive factors which, when administered in an effective amount to a subject mammal which is subsequently sensitized to a particular alloantigen, selectively suppress the DTH response in that mammal to that particular alloantigen. According to one preferred embodiment, the mammalian cells, preferably epidermal cells, are placed in suspension in a non-toxic, nutritive medium. While in suspension, the cells are irradiated with UV-radiation having a pre-determined wavelength. The source of the UV-radiation may be, for example, any commercially available "sunlamp," generating UV-radiation in pre-determined wavelengths. In one preferred embodiment, FS-40 sunlamps, Westinghouse (Bloomfield, N.J.) provided UVB-radiation. In another preferred embodiment, Dermalight 2001, (Dermalight Systems, Studio City, Calif.) provided UVA-radiation. The UV-radiation administered to the cells must be sufficient to result in UV-irradiated cells which produce immunosuppressive factors. Preferably, the amount of radiation administered to the cells is from about 10 to about 200 $J/m^2$, and most preferably from about 10 to about 40 $J/m^2$. The immunosuppressive factors are preferably secreted by the cells into the nutritive media. The immunosuppressive factors are thereafter extracted from the UV-irradiated cells. This extraction step may simply be the process of separating the UV-irradiated cells from the nutritive media. However, any known separation technique can be employed in the practice of the inventive method. The immunosuppressive factors may also, prior to administration, be concentrated by techniques well known in the art. Thereafter, a therapeutically effective amount of the immunosuppressive factors are administered to a mammal. According to one preferred embodiment, the therapeutically effective amount of the immunosuppressive factors is determined by the subject's physician (or veterinarian if the subject is an animal) as that amount of immunosuppressive factor required to suppress the particular immune response to the particular alloantigen. Most preferably, however, the therapeutically effective amount is that amount which prevents the occurrence of a particular pathology related to a specific alloantigen. The administration of the immunosuppressive factors may be as a single or divided dose. The immunosuppressive factors are preferably administered by injection, for example, intraperitoneally, subcutaneously, intramuscularly or intravascularly. However, the immunosuppressive factors are most preferably administered by intravenous injection or infusion.

The subject mammal is thereafter sensitized to the particular alloantigen for which immunotolerance is sought. According to one preferred embodiment, epidermal cells derived from a skin graft comprise the alloantigen and are used to sensitize the subject mammal to produce immunotolerance to the later transplanted skin graft, generally referred to as an allograft. According to a second preferred embodiment, spleen cells are used to sensitize the subject mammal. In this embodiment the epidermal cells or the spleen cells (alloantigens) may have substantially identical antigenic profiles as the later transplanted graft (allograft).

The inventive methods of the present invention are directed toward treating or preventing an occurrence of an immunologically-related pathology. In one embodiment, the immunologically-related pathology is graft vs. host disease, or host vs. graft disease, e.g., transplant rejection.

In another embodiment, the immunological-related pathology is the DTH response to a particular alloantigen. In yet another embodiment, the immunological-related pathology is the CHS response to a particular antigen. In general, the immunological-related pathology is a pathological condition for which the suppression of a specific alloantigen would be particular alloantigen would be beneficial.

The immune response to allogeneic histocompatibility antigens can be suppressed by injecting allogeneic spleen cells into mice that have been previously exposed to UV radiation. The suppression is mediated by antigen-specific suppressor T cells found in the spleens of the UV-irradiated mice. A previously unanswered question is, how does the irradiation of the animal's dorsal skin lead to the induction of splenic antigen specific suppressor cells? Findings of the present invention suggest that soluble factors released by UV-irradiated keratinocytes are involved in the induction of antigen-specific suppressor cells. Injection of culture supernatants from UV-irradiated keratinocytes into normal mice mimicked the effect of whole-body UV irradiation and suppressed the induction of delayed type hypersensitivity to alloantigen. Furthermore, spleen cells from these mice were unable to respond to the alloantigen in the mixed lymphocyte response. Antigen-specific suppressor T cells ($CD3^+$ $CD4^+$ $CD8^-$, radiation resistant) were found in the spleens of the mice injected with suppressive supernatants. The production of the suppressive cytokine is not inhibited by indomethacin treatment of the keratinocytes, suggesting the prostaglandins are not involved. Inhibition of protein synthesis with cycloheximide or treatment of the supernatants from the UV-irradiated keratinocytes with trypsin removes all suppressive activity suggesting the active material is a protein. Since the suppression of the immune response to alloantigen induced by this suppressive cytokine mimics the suppression found after exposure to UV radiation, these findings support the concept the induction of systemic suppression by UV radiation results from the release of suppressive substances by UV-irradiated keratinocytes. In addition, these data also suggest the induction of antigen-specific suppressor cells by this factor (a glycoprotein being induced by UVB irradiation) may provide a novel method of suppressing allograft rejection.

A unique feature of the suppression induced by UV radiation is that while Delayed Type Hypersensitivity (DTH) is suppressed, other immune responses such as antibody production remain normal. The selective nature of the UV-induced suppression is similar to the biological activity of Cytokine synthesis inhibition factor (IL-10). An aspect of the present invention is that IL-10 is secreted by keratinocytes (KC) following UV exposure leading to a down regulation of T helper 1 cell activity and suppression of DTH. To determine if IL-10 mRNA was present in UV-irradiated KC a probe was synthesized according to the published sequence of IL-10. (Moore, K. W., et al., 1990) KC monolayers (PAM 212 cells) were irradiated with UVB at specific times after exposure (0.5 to 24 hr). RNA from these cultures and mock-irradiated cells was extracted and screened by northern analysis. IL-10 mRNA was enhanced in UV-irradiated KC. The secretion of IL-10 by UV-irradiated KC was determined by western analysis. Supernatants (SN) from UV and mock-irradiated KC were electrophoresed via SDS-PAGE under reducing conditions. The material was electroblotted onto nitrocellulose and probed with an antibody specific for IL-10. Development of the blot revealed that IL-10 was released by UV-irradiated KC. IL-10 biological activity was determined by the ability of the SN to depress γIFN production by antigen-activated T helper 1 cells. SN from UV-irradiated KC caused a significant decrease of γIFN production whereas the addition of the SN from mock-irradiated KC was not suppressive. An aspect of the present invention is that UV-exposed KC produce a cytokine that exerts IL-10 biological activity. The release of KC-derived IL-10 is involved in the systemic suppression caused by UV radiation.

The following examples are included to further describe the present invention and are not intended to limit the invention unless otherwise specifically indicated herein.

Material and Methods for Examples 1–3

Mice

Specific pathogen-free females C3H/HeN Cr (MTV-) and BALB/AnN mice were supplied by the NCI-Frederick Cancer Research Facility, Animal Production Area (Frederick, Md.) The animals were housed and cared for according to the guidelines set forth in The Guide For The Care And Use Of Laboratory Animals, (DHHS Publication No. [NIH] 78-23), in a facility fully accredited by the American Association for the Accreditation of Laboratory Animal Care, and their use was approved by the Institution Animal Care and Use Committee.

Exposure Of Mice To UV Radiation

The dorsal fur of the mice was removed by shaving with electric clippers. The mice were then exposed for 3 hrs. to UVB (280 nm–320 nm) radiation provided by a bank of 6 FS-40 sunlamps (Westinghouse, Bloomfield, N.J.). Approximately 70% of the radiation emitted by these lamps is within the UVB range. The irradiance of the source averaged 10 W/m$^2$, as measured by an IL-700 radiometer, using a PT171C UVB detector equipped with a UVB 320 filter and A127 quartz diffuser (International Light, Inc., Newburyport, Mass.). Due to shielding by the cage lids the incident dose received by the animals was approximately 4.5 W/m$^2$. The total dose of UV received was approximately 40 kJ/m$^2$. During irradiation the ears of the mice were covered with tape to prevent damage from the UV radiation.

In vitro UV-irradiation of epidermal cell cultures

Epidermal cell suspensions were prepared from the ears and trunk skin of mice. The fur was removed by shaving and the skin was removed and cut into 1 mm$^2$ pieces. These were floated at 37° C. in 0.75% trypsin/EDTA. After 60 minutes the epidermis was separated from the dermis by teasing apart with forceps. The epidermis was cut into small pieces and stirred for 30 minutes in 0.25% trypsin/EDTA. The resulting cell suspension was filtered through nylon mesh, counted and resuspended to 1×10$^6$ cell/ml in minimal essential media (MEM) supplemented with; 5% fetal calf serum, 2 mM glutamine and 1% non-essential amino acids (Gibco Laboratories, Grand Island, N.Y.). Five ml of the cell suspension was added to 100 mm tissue culture dishes. Twenty-four hours later the non-adherent cells were removed and the monolayers resuspended in PBS and irradiated with 200 J/m$^2$ of either UVA or UVB radiation. The source of the UVB radiation was a single FS-40 sunlamp with an output of 1.43 W/m$^2$, at a tube to target distance of 20 cm. This lamp emits a continuous spectrum from 270 nm to 390 nm with peaks at 313 nm and 365 nm. Approximately 70% of the energy emitted by this lamp was within the UVB region. The source of the UVA radiation was a Dermalight 2001 equipped with an optical filter (H-1) to remove contaminating UVB (Dermalight Systems, Studio City, Calif.). Essentially all the radiation (99.5%) emitted by this lamp was within the UVA range as determined with an Optronics 742 Spectroradiometer (Optronic Laboratories Inc., Orlando, Fla.). The output of this lamp was 56 W/m$^2$ at a tube to target distance of 20 cm. Immediately after irradiation, the cells were washed 3 times with PBS and resuspended in serum free MEM. Eighteen to 24 hours later the supernatant (UVB-SN or UVA-SN) from the cultures was removed and passed through 0.22 micron filters. In some of the experiments the keratinocyte line, PAM 212 (Yuspa, 1980) was used. The cells were adjusted to 1×10$^6$ cells/ml and 5 ml of the cell suspension was plated in 100 mm tissue culture dishes. Twenty-four hours later these cells were irradiated as described above. The cells were resuspended in serum-free MEM and the supernatants obtained 18 to 24 hours later. Control supernatants (NR-SN) were obtained from cells treated in an identical manner but not exposed to UV radiation.

Effect Of Supernatants From The UV-Irradiated Epidermal Cells On CHS

Mice were injected via the tail vein with 0.5 ml of UVA-SN, UVB-SN or NR-SN. Five days later the animals were sensitized by the epicutaneous application of trinitrochlorobenzene (TNCB, 100 ul of a 3% w/v solution is acetone) or dinitrofluorobenzene (DNFB, 50 ul of a 0.3% v/v solution in acetone) on the shaved abdominal skin. Six days later the mice were challenged by applying 5 ul of a 1% solution of TNCB or a 0.2% solution of DNFB onto each ear surface. The thickness of the pinna of each ear was measured with a spring loaded micrometer (Swiss Precision Instruments, Los Angeles, Calif.) immediately prior to challenge and 24 hours later. The background response was determined by measuring the swelling found in animals that were not sensitized but were challenged. The specific swelling was calculated by subtracting the background swelling from that seen in the experimental groups. There were 5 mice per group.

Effect of supernatants from the UV-irradiated cells on DTH

BALB/C mice were injected via the tail vein with 0.5 ml of UVB-SN, UVA-SN or the control, NR-SN. Five days later these mice were sensitized with allogeneic C3H spleen cells by injecting 2.5 ×10$^7$ cells into each flank. Six days later the mice were challenged with C3H spleen cells by injecting 10$^7$ cells into each hind footpad. The resulting footpad swelling was read 24 hours later. As before, the background swelling was determined by challenging non-sensitized mice with C3H cells, and the specific swelling was calculated by subtracting the background swelling from the footpad swelling of the experimental groups. There were 5 mice per group.

Alternatively, BALB/c mice were sensitized with 5×10$^7$ syngeneic spleen cells modified with the trinitrophenol (TNP) hapten as described by Shearer (1974). Six days later these mice were challenged by injecting 10$^7$ TNP-conjugated spleen cells into each hind footpad. Twenty-four hours later the footpad swelling was determined.

Determination of antibody production

The slide modification (Mishell and Dutton, 1967) of the Jerne and Nordin (1963) plaque assay was used. Mice were injected with 0.5 ml of UVB-SN, UVA-SN or NR-SN and 5 days later were immunized by the intravenous (iv) injection of a 1% solution of sheep erythrocytes (SRBC). Five days after immunization, the spleens of the mice were removed and the number of direct plaque-forming cells was determined by using SRBC or horse erythrocytes (HRBC) as the indicator cells.

Statistical Analysis

A multiple comparison procedure employing a one way analysis of variance was used to determine statistical significant differences between experimental and control groups (Dunnett, 1985).

Probabilities less than 0.05 were considered significant.

Representative experiments are shown; each experiment was repeated at least twice with similar results.

EXAMPLE 1

Figure 1B:
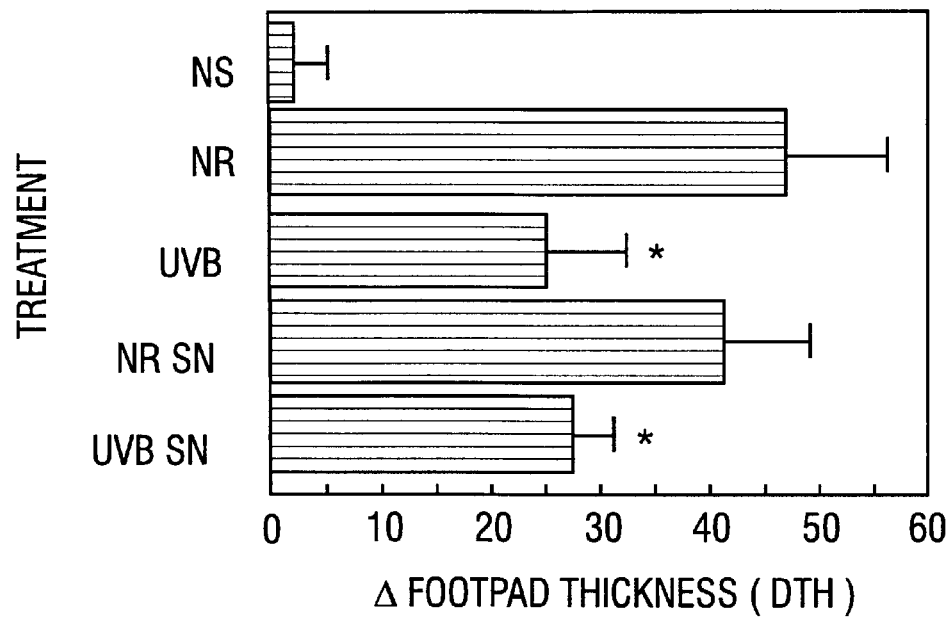

Suppression of DTH but not CHS after the Injection of Supernatants from UVB-Irradiated Epidermal Cells Primary epidermal cell cultures were prepared from the back skin and ears of C3H mice. The cultures were exposed to 200 J/m² of UVB radiation and 24 hours later the supernatants from these cultures were injected into normal mice. Five days later half of the mice were sensitized with TNCB and the other half injected with Balb/c spleen cells. Six days later the mice were challenged with the respective antigen and the CHS and DTH response measured 24 hours later. As controls for the experiment, two groups of mice were also irradiated with 40 kJ/m² of UVB-radiation (whole body irradiation). As can be seen in FIG. 1A and FIG. 1B, exposure to whole-body UVB radiation (UVB) suppressed both the generation of CHS (panel A) and DTH (panel B) when compared to the non-irradiated control (NR, P<0.001). The injection of the UVB-SN also suppressed DTH (FIG. 1B). Contrary to expectations, the injection of the UVB-SN had no significant effect on CHS (FIG. 1A). The injection of the control supernatant (NR-SN) had no suppressive effect on CHS or DTH.

Figure 2A:
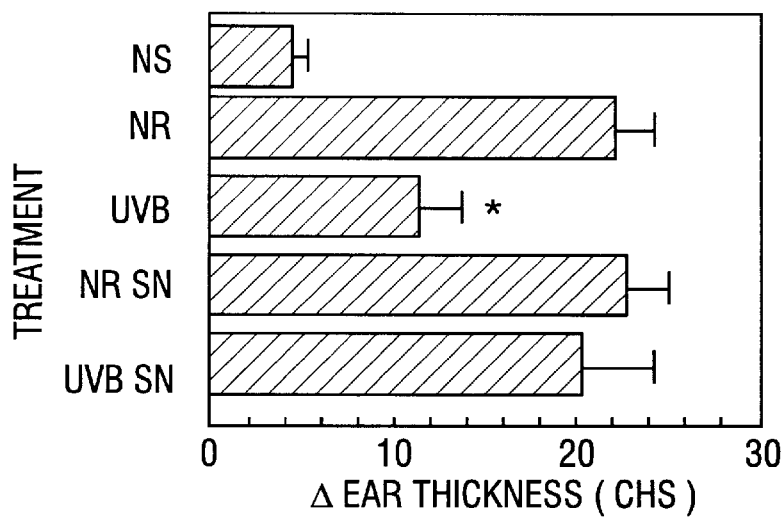
FIG. 2A and FIG. 2B shows the effect of the supernatants from UV-irradiated Pam 212 cells on the induction of CHS(A) or DTH(B). Mice were injected with supernatants from the UV-irradiated (UVSN) or control (NRSN) non-irradiated keratinocyte cell cultures or exposed to 40 kJ/m$^2$ of UVB radiation (UVB). In panel A, Balb/c mice were sensitized with TNCB, in panel B, Balb c mice were sensitized with C3H spleen cells. The asterisk indicates a significant difference (P<0.001) from the response observed in the positive control (NR). The background response was measured in mice that were challenged but not sensitized with the antigen (NS). There were 5 mice per group; units=cm×$10^{-3}$.
Figure 2B:
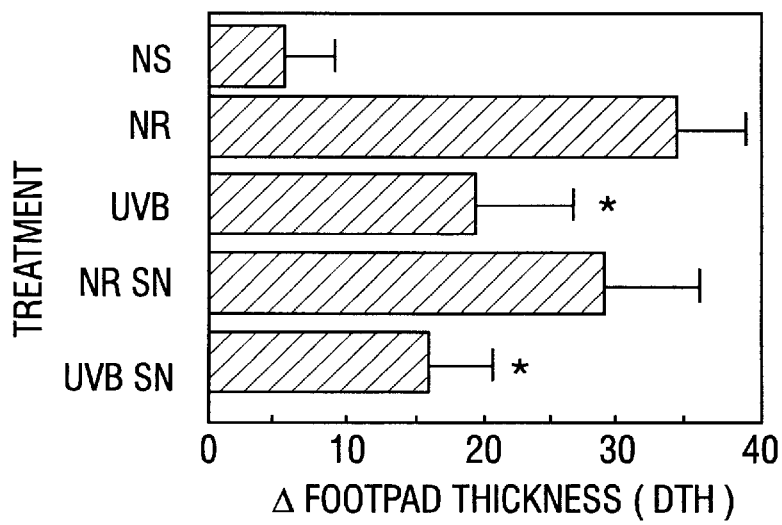

A keratinocyte line, Pam 212, was also used as a source of potentially immunosuppressive supernatants. The effect that the injection of these supernatants had on the generation of CHS and DTH is shown in FIG. 2A and FIG. 2B. As before, the control for this experiment consisted of exposing mice to 40 kJ/m² of UVB radiation. There was a significant suppression (P<0.001) of both CHS and DTH after whole-body UVB radiation (UVB) when compared to the immune response generated in unirradiated animals (NR). When the UVB-SN was injected into BALB/c mice that were subsequently sensitized with TNCB, it had no suppressive effect (FIG. 2A). When, however, the same UVB-SN was injected into BALB/c mice that were subsequently injected with C3H spleen cells, DTH to the alloantigen was significantly suppressed (P<0.001) (see FIG. 2B). The injection of supernatants from non-irradiated Pam 212 cells (NR-SN) had no suppressive effect. This experiment was repeated using two other contact allergens, dinitrofluorobenzene and oxazofone. In both cases the UVB-SN, generated by irradiating Pam 212 cells with UVB radiation had no suppressive effect on CHS.

Figure 3:
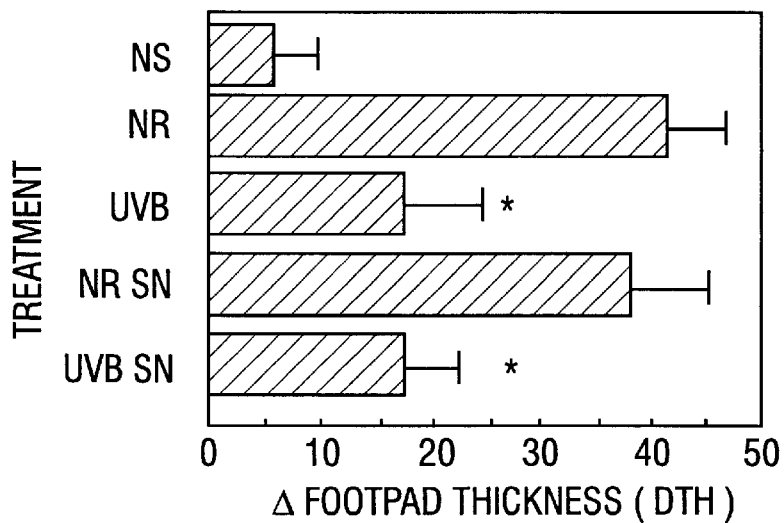
FIG. 3 shows the effect of the supernatants from UVB-irradiated Pam 212 cells on the induction of DTH to TNP-conjugated syngeneic spleen cells. Mice were injected with supernatants from the UVB-irradiated (UVB-SN) or control (NR SN) keratinocyte cell cultures or exposed to 40 kJ/m$^2$ of UV radiation (UV). The asterisk indicates a significant difference (P<0.001) from the response observed in the positive control (NR). The background response was measured in mice that were challenged but not sensitized with the TNP-conjugated normal spleen cells (NS). There were 5 mice/group: units=cm×$10^{-3}$.

The above data demonstrated that the immunosuppressive factors generated from the UVB-irradiated epidermal cells suppress DTH but not CHS. The effect that injection of UVB-SN had on the DTH response to a different antigen was also examined. TNP-conjugated syngeneic spleen cells were used as the antigen. Supernatants from UVB-irradiated and non-irradiated Pam 212 cells were injected into Balb/c mice. These mice were then sensitized and challenged with TNP-conjugated Balb/c spleen cells, not an allogeneic histocompatibility antigen. The data from this experiment is summarized in FIG. 3. Compared to the non-irradiated control (NR), both the injection of the UVB-SN and exposure of the mice to whole-body UVB-radiation (UVB), resulted in a significant (P<0.001) suppression of DTH to TNP-modified spleen cells. This data indicated that, regardless of the antigen used, supernatants generated by exposing epidermal cells to UVB suppress DTH but not CHS.

Contrary to the results published by Schwarz and colleagues, the supernatant released from UVB-irradiated epidermal cells was unable to suppress CHS. In Schwarz et al. (1986) the source of the UVB-radiation used was an Osram Vitalux bulb emitting a continuous spectrum between 300 nm and 600 nm, with peaks at 310 nm and 390 nm. The FS-40 lamp used in the present invention has a continuous spectrum of from about 270 nm to 390 nm, with peaks at 312 nm and 365 nm. Thus, Schwarz and colleagues appear to have used a considerable amount of UVA in the generation of their suppressor factor and, as demonstrated herein, UVA-radiation of cells generated a factor which selectively suppresses CHS while UVB-radiation generates a factor that selectively suppresses DTH.

EXAMPLE 2

Suppression of CHS but not DTH by Factors Released from UVA-Irradiated Keratinocytes Separate Pam 212 cultures were irradiated with 200 J/m² of either UVB or UVA radiation. Twenty-four hours later, 0.5 ml of each supernatant as well as 0.5 ml of the control supernatant from non-irradiated cultures was injected into various groups of mice. Five days later one half of the mice were sensitized with DNFB and the other half were injected with allogeneic spleen cells. Six days after sensitization the mice were challenged with the appropriate antigen and the resulting DTH and CHS reactions were measured one day later. The data from this experiment are summarized in Table 1.

TABLE 1

EFFECT OF SUPERNATANTS FROM UVA AND UVB-IRRADIATED PAM 212 CELLS ON CHS AND DTH

| | Treatment[a] | Ear[b] Thickness (±SEM) | Specific[c] Swelling | %[d] Suppression | P[e] |
|---|---|---|---|---|---|
| CHS | None | 3 ± 1 | 0 | — | |
| | NR | 16 ± 4 | 13 | 0 | — |
| | NR-SN | 14 ± 6 | 11 | 15 | NS |
| | UVA-SN | 9 ± 2 | 6 | 54 | 0.002 |
| | UVB-SN | 12 ± 3 | 9 | 31 | NS |

| | Treatment[a] | foot pad[b] thickness (±SEM) | specific[c] swelling | %[d] suppression | P[e] |
|---|---|---|---|---|---|
| DTH | None | 3 ± 3 | 0 | — | |
| | NR | 31 ± 5 | 28 | 0 | — |
| | NR-SN | 29 ± 7 | 26 | 8 | NS |
| | UVA-SN | 25 ± 5 | 22 | 21 | NS |
| | UVB-SN | 19 ± 3 | 16 | 43 | 0.002 |

[a]Mice were injected with 0.5 ml of supernatant from Pam 212 cultures exposed to 200 J/m² of UVA (UVA-SN) or UVB (UVB-SN) radiation, or with 0.5 ml of supernatant from non-irradiated cells (NR-SN). The response in these mice was compared to the response of the control animals (NR). In the CHS experiment the mice were sensitized with DNFB, in the DTH experiment the mice were injected with allogenic spleen cells.
[b]Units - cm × 10⁻³; 5 mice per group.
[c]The background swelling found in the non-sensitized control mice was subtracted from the swelling found in the experimental groups.
[d][1 − (specific swelling of experimental group/specific swelling of control group)] × 100.
[e]P values were determined by a one way ANOVA:NS = not significantly different from the NR control (P > 0.05)

As before, the injection of supernatants from the non-irradiated cells (NR-SN) had no significant effect on the magnitude of the CHS response (compare normal mice (NR) to NR-SN, P>0.05). While the injection of the supernatant from the UVB-irradiated Pam 212 cells (UVB-SN) resulted in a minimal level of CHS suppression there was no significant difference between these two groups (NR vs UVB-SN, P>0.050). However, when the supernatant from UVA-irradiated cells (UVA-SN) was injected into mice there was a significant suppression of the CHS response (NR vs UVA-SN, P<0.002).

The opposite situation was observed when DTH was measured. The DTH response found after the injection of the supernatant from the non-irradiated cells (NR-SN) or the supernatant from the UVA-irradiated cells (UVA-SN) was indistinguishable from the control (NR vs NR-SN and NR vs. UVA-SN, P>0.05). But as shown previously, the injection of the supernatant from the UVB-irradiated Pam 212 cells (UVA-SN) resulted in a significant suppression of the DTH response to the alloantigen (NR vs UVB-SN, P<0.002). This data demonstrated that at least two factors are released from UV-irradiated keratinocytes, one triggered by UVA radiation that suppresses CHS and the second, triggered by UVB radiation, that suppresses DTH.

EXAMPLE 3

Effect of UVB-SN on Antibody Production

Mice were injected with the UVB-SN produced as described in Example 2 or exposed to 40 kJ/m$^2$ of UVB-radiation. Five days later they were injected with 0.1 ml of a 1% solution of SRBC via the tail vein. Five days after this immunization, their spleens were removed and the numbers of antibody-forming cells were determined. This experiment is summarized in Table 2.

TABLE 2

EFFECT OF THE SUPERNATANT FROM UVB-IRRADIATED PAM 212 CELLS ON ANTIBODY FORMATION

| Treatment[a] | Anti-SRBC PFC/10$^6$ spleen cells[b] (±SEM) |
|---|---|
| + HRBC | 0 |
| + SRBC | 1144 ± 90 |
| UVB + SRBC | 1052 ± 42 |
| UVB-SN − SRBC | 1081 ± 78 |
| NR-SN + SRBC | 1317 ± 68 |

[a]Mice were exposed to 40 kJ/m$^2$ of UV radiation (UVB) or injected with supernatant from UVB-irradiated primary epidermal cell cultures (UVB-SN) or supernatant from the non-irradiated control (NR-SN). These mice were then injected with sheep erythrocytes. The number of plaque-forming cells (PFC) was determined by using SRBC as the indicator cells. The response of normal mice immunized with sheep erythrocytes (+SRBC) wascompared to the response found in mice exposed to UVB or injected with supernatants from the epidermal cell cultures. The background response was determined by injecting mice with horse erythrocytes (+HRBC) and measuring the number of anti-SRBC plaques.
[b]There were 2 mice per group. Each spleen was assayed individually, 3 slides per spleen. The data represents the mean values from six slides.

There was no significant effect on antibody formation by either total-body exposure to UVB-radiation, or injection of the UVB-SN suppressive supernatants. This demonstrated that the suppression induced by the immunosuppressive factor, like the suppression induced by total body exposure to UVB radiation, is selective.

Material and Methods for Examples 4–9

Mice

Pathogen-free female C3H/HEN (MTV-) BALB/c and C57BL/6 mice were obtained from the National Cancer Institute, Frederick Cancer Research Facility Animal Production Area. The mice were cared for according to the guidelines set forth in the Guide for the Care and Use of Laboratory Animals (DHHS Publication No. [NIH] 78-23) in an AAALAC accredited animal facility and their use was approved by the Institutional Animal Care and Use Committee.

Treatment of Mice with UVB-Radiation

Mice were exposed to UVB (280–320) radiation provided by a bank of 6 FS-40 sunlamps (Westinghouse, Bloomfield, N.J.). The spectral output of the FS-40 bulbs as well as the method used to irradiate the mice have been described in detail in the Materials and Methods for Examples 1–3.

Effect of UVB on Allograft Rejection

Recipient BALB/c mice were irradiated with 40 kJ/m$^2$ on day 0. During the irradiation their ears were covered with tape to prevent damage. Five days later, the mice were sensitized with antigen by injecting 5×10$^7$ C3H spleen cells subcutaneously. One week later, C3H heart fragments were implanted into the ears of the recipient mice according to the procedure of Klein et al. (1986). Survival of each graft was scored by visual examination of pulsating tissue. Grafts were first scored at 5 days (at which time 100% were viable), and then scored every 2–3 days afterward.

Induction of Graft versus Host Disease (GVHD)

GVHD was induced by using the procedure of Korngold and Sprent (1985). Lethally X-irradiated (850 rads) BALB/c mice were reconstituted with 5×10$^6$ T cell-depleted C3H bone marrow cells (ATBM, antiThy 1.2 clone 30-H12, Becton Dickinson, Mountain View, Calif., plus complement) and 5×10$^5$ C3H spleen cells. Spleen cells were obtained from normal C3H mice, C3H mice exposed to 40 kJ/m$^2$ UVB, C3H mice exposed to UVB and sensitized with 5×10$^7$ BALB/c spleen cells 5 days after UVB exposure, and C3H mice sensitized with 5×10$^6$ BALB/c cells. Spleen cells and allogeneic T cell-depleted bone marrow (ATBM) were injected into the recipient mice via the tail vein. The recipient BALB/c mice were maintained on autoclaved food, bedding, and antibiotic-supplemented water. The animals were checked daily for morbidity and mortality.

Effect of UVB on Tumor Allograft Rejection

C3H mice were exposed to 40 kJ/m$^2$ of UVB-radiation, and 5 days later sensitized by the subcutaneous injection of 5×10$^7$ mitomycin C-treated (50 ug/ml) B16 melanoma cells (Fidler, 1973). One week later, these mice were challenged with 2×10$^6$ VIABLE B16 CELLS. At the same time, one group of normal c57BL/6 mice was challenged with an equivalent number of B16 cells. In addition, BALB/c mice were also exposed to UVB and sensitized with 5×10$^7$ mitomycin C-treated UV2237 cells (a progressor UV-induced tumor generated in C3H mice (Kripke, 1977)). One week after sensitization, the mice were challenged with 2×10$^6$ viable UV2237 cells. As a control normal, C3H mice were also injected with two million UV2237 cells.

Mixed Lymphocyte Cultures

Spleen cells were removed from C3H mice that were exposed to UVB and sensitized with BALB/c cells or from nonirradiated mice that were sensitized with BALB/c cells and single-cell suspensions were prepared. Erythrocytes were lysed with ammonium chloride and the cells were washed and resuspended in RPMI1640 medium (Ullrich, 1986). Generally, 2×10$^5$ gamma-irradiated (5000 rads) stimulator cells were incubated in 96-well round-bottomed microliter plates. The cells were cultured for 5 days at 37° C., during the last 6 hrs of culture, 1 uCi/well of tritiated thymidine (ICN Radiochemicals, Irvine, Calif.) was added. The incorporation of the radioisotope by the responder cells was measured by harvesting the cells onto glass fiber filters, followed by liquid scintillation counting.

Depletion of Lymphocyte Subsets by Monoclonal Antibody and Complement Treatment The methods used to deplete lymphocyte subsets with specific monoclonal antibodies and complement have been described (Ullrich and Kripke, 1984; Ullrich, 1986). The antibodies used were: anti-Thy 1.2 (clone 30-H12, Becton Dickinson, Mountain View, Calif.), anti-Lyt-1 and Lyt-2 (New England Nuclear, Boston, Mass.), anti-L3T4a (clone GK-15), and anti-IJ$^k$ (clone WF8c.12.8). The anti L3T4a and anti I–J$^k$ were obtained from the Dept. of Immunology, M.D. Anderson Hospital, Houston, Tex.

EXAMPLE 4

Relationship between Exposure to UVB and Resulting Immunosuppression

Figure 4:
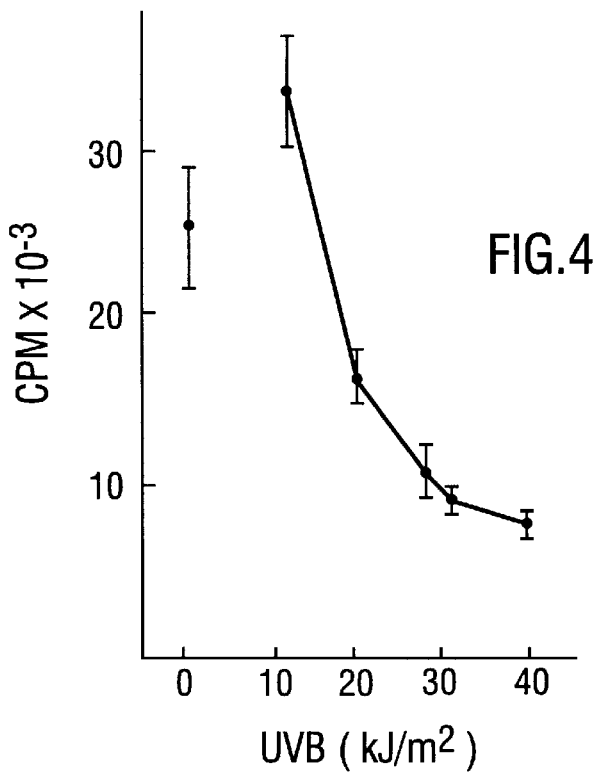
FIG. 4 shows the relationship between the suppression of MLR and the dose of UVB given. Mice were exposed to various doses of UVB and sensitized with 5×10$^7$ allogeneic cells. Cells from these mice were cultured in an MLR, and their response was compared with the response observed when cells were isolated from nonirradiated antigen-sensitized mice.

FIG. 4 shows the relationship between the dose of UV given and the resulting suppression. The proliferation of spleen cells taken from C3H mice that were exposed to various doses of UVB and then sensitized with alloantigen was measured. This proliferation was compared with the response observed when spleen cells were isolated from C3H mice that were not exposed to UVB but were sensitized with alloantigen. The data presented in FIG. 4 demonstrate that, as the dose of UVB given was decreased, the resulting suppression decreased. This showed a direct relationship between the degree of suppression and the exposure to UVB. Based on these data, a 40 kJ/m$^2$ exposure to UVB was used in the following experiments.

EXAMPLE 5

Effect of Exposure to UVR on the Rejection of Allogeneic Heart Grafts

Recipient BALB/c mice received one of 4 treatments. The first group was the normal control, the second group was exposed to UVB, the third group was exposed to UVB and sensitized with C3H spleen cells, and the fourth group was the nonirradiated (NR) control that had been sensitized with C3H spleen cells. Seven days after sensitization, newborn C3H heart fragments (allografts) were implanted in the left ears of the BALB/c mice. As demonstrated in Table 3 there was a significant prolongation of graft survival in mice exposed to UVB and sensitized with alloantigen (P<0.001, Wilcoxon rank sum test).

TABLE 3

PROLONGATION OF ALLOGRAFT SURVIVAL AFTER UVB TREATMENT AND ANTIGENIC SENSITIZATION OF THE RECIPIENT

| | Survival of heart grafts* | |
|---|---|---|
| Treatment of recipient | MST (days) | RANGE |
| control | 5 | 5–7 |
| UVB | 5 | 5–7 |
| UVB + C3H spleen cells | 14** | 7–28 |
| C3H spleen cells | 5 | 5–7 |

*Survival of each graft was scored by visual examination of pulsating tissue using a stereomicroscope at 10 × magnification. Grafts were first scored at 5 days and then scored every 2–3 days afterward. Control BALB/c heart fragments were implanted into each right ear; an MST of >days was observed. There were 10 mice in each group.
**P < .001, Wilcoxon rank-sum test.

Exposure of the recipients to UVB alone, or sensitization with the alloantigen only, did not prolong the survival of the allografts when compared with the normal control. As an additional control for this experiment, BALB/c hearts were placed into the right ears of these mice. The median survival time (MST) of these grafts was greater than 60 days.

EXAMPLE 6

The Specificity of UVB Suppression

C57BL/6 mice were exposed to UVB and sensitized with either BALB/c or C3H spleen cells. Seven days after sensitization a BALB/c heart fragment (allograft) was implanted into one ear and a C3H heart fragment was implanted into the other. The survival of the allografts was compared with the mean survival time (MST) of heart fragments transplanted into a normal animal. The results from this experiment, as summarized in Table 4, demonstrate that allograft survival is prolonged only when the allograft is syngeneic to the antigen used to sensitize the UV-irradiated animal.

TABLE 4

SPECIFICITY OF THE SUPPRESSION OF ALLOGRAFT REJECTION$^a$

| | Survival of heart grafts (MST [range]) | |
|---|---|---|
| Treatment of recipients | BALB/c | C3H |
| UVB + BALB/c | 14 (14–21)$^b$ | 5 (5–7) |
| UVB + C3H | 7 (5–7) | 14 (7–21)$^b$ |
| None | 5 (5–7) | 5 (5–7) |

$^a$Recipient C57BL/6 mice were exposed to UVB radiation and sensitized with either BALB/c or C3H spleen cells. At one week following sensitization C3H heart fragments were implanted in the left ear and BALB/c heart fragments were implanted in the right ear. There were five mice in each group.
$^b$P < .001 vs. the normal controls.

EXAMPLE 7

Suppression of Tumor Allograft Rejection by UVB and Alloantigenic Sensitization

Another measure of the immune response to alloantigens is the ability to reject tumor allografts. The effect that UVB and alloantigenic sensitization had on tumor allograft rejection was measured by the following experiment. The mice were separated into four groups, the normal control, UVB-irradiated only, UVB-irradiated and sensitized with alloantigen, and alloantigen sensitized only. These mice were then challenged with the allogeneic tumors. As demonstrated in Table 5, the allogeneic tumors were all rejected by the normal mice.

TABLE 5

SUPPRESSION OF TUMOR ALLOGRAFT REJECTION BY THE ANTIGENIC SENSITIZATION OF UV IRRADIATED MICE

| Treatment of recipients C3H | | Tumor incidence (B16) | Treatment of recipients BALB/c | | Tumor incidence (UV2237) |
|---|---|---|---|---|---|
| UVB$^a$ | Sensitization$^b$ | | UVB$^a$ | Sensitization$^c$ | |
| – | – | 0/5$^d$ | – | – | 0/10$^d$ |
| + | – | 0/5 | + | – | 0/10 |
| – | B16 | 0/5 | – | UV2237 | 0/10 |
| + | B16 | 4/5 | + | UV2237 | 6/10$^e$ |

$^a$Mice were exposed to 40 kJ/m$^2$ of UVB on the shaved dorsal skin.
$^b$5 × 10$^7$ mitomycin C-treated B16 cells, 5 days after irradiation.
$^c$5 × 10$^7$ mitomycin C-treated UV2237 cells, 5 days after irradiation.
$^d$5 × 10$^7$ mitomycin C-treated UV2237 cells, 5 days after irradiation.
$^e$P < .01 vs nonirradiated sensitized mice, chi-square test; 100% of normal C57BL/6 control mice injected with B16 and 80% of normal C3H control mice injected with UV2237 developed tumors.

Treatment with UVB only or alloantigenic sensitization only had no effect on tumor rejection. However, when the mice were first exposed to UVB and then sensitized with the tumor alloantigen, the rejection of the tumors was suppressed, as evident by tumor growth in the allogeneic mice. To rule out the possibility that these results were due to the selection of antigenless variants, the tumors were excised and transplanted into normal mice. The B16 grew progressively in C57BL/6 mice but was rejected in C3H mice. Similarly, the UV 22327 grew in normal C3H mice but was rejected in normal BALB/c mice.

EXAMPLE 8

The effect of UVB and Alloantigenic Sensitization on GVHD

Figure 5:
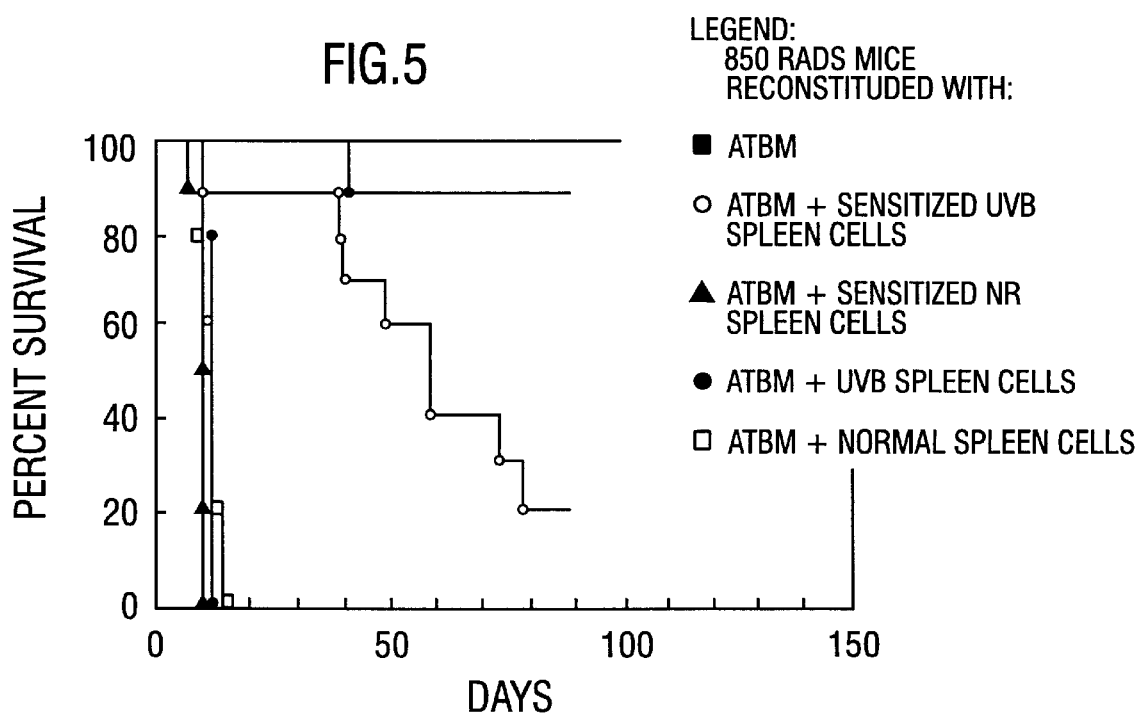
FIG. 5 shows the effect of UVB radiation and antigenic sensitization on GVHD. Lethally X-irradiated (850 rads) BALB/c mice were reconstituted with 5×10$^6$ T cell-depleted C3H bone marrow cells (ATMB), anti-Thy 1.2 monoclonal antibody, Becton Dickinson, Mountain View, Calif.: plus complement) and 5×10$^5$ C3H spleen cells. ATMB only (solid squares). Spleen cells were obtained from normal control mice (open squares); mice exposed to UVB only (solid circles); mice sensitized with alloantigen (solid triangles); or mice expose to UVB and sensitized with alloantigen (open circles). The animals were checked daily for morbidity and mortality. The experiments were terminated at 90 days. Statistical differences between the median survival times were determined by use of the Wilcoxon rank-sum test, P<0.001: ATBM+sensitized UVB spleen cells vs. ATBM+sensitized NR spleen cells, n=10.

The ability of UVB and alloantigenic sensitization to effect the survival of mice with lethal GVHD was examined. GVHD was induced by injecting lethally X-irradiated BALB/c mice with a mixture of T cell-depleted C3H bone marrow cells and mature C3H spleen cells (Korngold and Sprent, 1985). The question addressed was whether treatment of the spleen cell donors with UVB followed by alloantigenic sensitization could induce a state of suppression that would inhibit the reaction of the graft against the host. The donor mice received one of four treatments, the normal control, UVB only, UVB plus alloantigenic sensitization, and sensitization only. Seven days after sensitization, spleen cells from these mice plus allogenic T-cell depleted bone marrow (ATBM) were injected into the BALB/mice. As shown in FIG. 5, when the BALB/c mice were reconstituted with ATBM only, an MST greater than 90 days was observed. Injection of normal spleen cells with the ATBM resulted in the induction of GVHD with an MST of 12 days. The use of spleen cells from mice exposed only to UVB (UVB spleen cells) or from mice sensitized only with antigen (sensitized UVB spleen cells) did not alter the MST. When, however, the spleen cells were obtained from C3H mice that were first exposed to UVB and then sensitized with BALB/c cells (sensitized UVB spleen cells), a significant prolongation of the MST was observed.

A major problem in bone marrow transplantation is the induction of GVHD. Methods of reducing GVHD generally include histocompatibility matching between the donor and recipient, the use of immunosuppressive drugs, and the removal of T cells from the graft (Storb, 1987). Using a method of the present invention a significant prolongation of survival was achieved when spleen cells from UVB-irradiated antigen-sensitized mice were transferred to recipients that differed across major histocompatibility barriers, in the absence of any immunosuppressive drugs. The methods of the present invention yield another method of reducing the incidence of GVHD.

EXAMPLE 9

UV-Induced Suppressor Cells are Responsible for the Suppression of the Immune Response to Alloantigens The present inventor has previously shown that antigen-specific suppressor cells (possibly T-lymphocytes) are present in the spleens of the ultraviolet-irradiated alloantigen sensitized mice (Ullrich and Magee, 1988). To establish identity of these suppressor cells, cells from the UV-treated antigen-sensitized mice were treated with anti-Thy 1.2 plus complement prior to adding them to a primary mixed lymphocyte reaction (MLR). As demonstrated by the data presented in Table 6, depletion of T cells from the suppressor cell population totally abrogated the suppressive effect.

TABLE 6

PHENOTYPE OF SPLEEN CELLS FROM UVB-TREATED MICE THAT SUPPRESS MLR

| Cells cultured[a] | CPM ± SEM[b] | %[c] Suppression | p[d] |
|---|---|---|---|
| C3H | 4,176 ± 1571 | | |
| C3H + BALB/c | 99,444 ± 7130 | 0 | |
| C3H + BALB/c + UVB | 20,251 ± 1288 | 80 | <.001 |
| C3H + BALB/c + NR | 102,703 ± 9017 | 0 | |
| C3H + BALB/c + aThy1.2UVB | 167,249 ± 26,073 | 0 | |
| C3H + BALB/c + aLyt1.1UVB | 135,026 ± 15,323 | 0 | |
| C3H + BALB/c + aLyt2.1UVB | 20,237 ± 3192 | 80 | <.001 |
| C3H + BALB/c + aIJ$^K$UVB | 102,529 ± 7303 | 0 | |
| C3H + BALB/c + aL3T4UVB | 112,043 ± 4687 | 0 | |
| C3H + BALB/c + aIgGUV | 55,358 ± 318 | 45 | <.002 |

[a]$2 \times 10^5$ C3H cells plus $2 \times 10^5$ mitomycin C-treated BALB/c cells were cultured with $2 \times 10^5$ nylon wool-purified spleen cells from UV-treated or NR control mice.
[b]Means values from triplicate cultures ± SEM.
[c](1 − [CPM C3H + BALB/c + UVB cells/CPM C3H ± BALB/c]) × 100.
[d]P value determined by two-tailed Student's t test; C3H + BALB/c vs. C3H + BALB/c + UVB cells.

In addition, depletion of Lyt $1^+IJ^{k+}$ and L3T4a$^+$ cells also removed the suppressive effect but depletion of Lyt $2^+$ or Ig$^+$ cells had no effect. These data demonstrate that the suppressor cells induced by alloantigenic sensitization of UVB-irradiated mice are indeed T-cells.

EXAMPLE 10

Suppression of the Immune Response to Alloantigen by Factors Released from UV-Irradiated Keratinocytes Exposure of mice to UV radiation followed by injection of allogeneic cells results in suppression of the immune response to alloantigen. Both the induction of delayed hypersensitivity (DTH) and the ability of spleen cells from UV-irradiated alloantigen-sensitized mice to proliferate to alloantigen in the mixed lymphocyte reaction (MLR) is suppressed (Ullrich S. E., 1986). The suppression is specific, sensitization of C3H mice with BALB/c cells after exposure to UV radiation suppresses the response of the C3H mice against BALB/c antigens, but the response of these mice against other alloantigens, such as C57B1/6 (B6) is not suppressed. Antigen-specific Thy 1.2+, Lyt 1+, 2− suppressor cells are found in the spleens of these mice. Two signals are required to induce the suppressor cells, the mice must be exposed to UV radiation and sensitized with alloantigen. Exposure to UV radiation alone or simple antigenic sensitization is not sufficient to induce suppression. Allograft rejection is also suppressed in mice exposed to UV and sensitized with alloantigen (Ullrich, S. E. and M. Magee. 1988). The ability to reject allogeneic heart fragments is significantly suppressed by treating the recipient mice with UV radiation. Here, also the suppression is specific, exposure of BALB/c mice to UV followed by injection of C3H spleen cells results in a prolonged survival of C3H heart fragments but not B6 heart fragments. The survival of the B6 hearts was similar to the survival found in non-irradiated normal controls. In addition, the ability of spleen cells from mice exposed to UV and sensitized with alloantigen to induce lethal graft versus host disease in x-irradiated allogeneic recipient mice was significantly suppressed (Ullrich, S. E. and M. Magee., 1988) these data demonstrate that UV exposure can be used to suppress the rejection of organ transplants. The major advantage in using UV exposure coupled with allogeneic sensitization to induce suppression is the antigen-specificity of the resulting suppressor cells.

An intriguing and not completely understood question about the suppression induced by UV radiation is: how are suppressor T cells induced? Clearly, the penetrating power of UV radiation is not sufficient to directly irradiate the cells of the spleen (Evertt, M. A. et al., 1966). One hypothesis is that a soluble photoproduct is released by the UV-irradiated epidermal cells that leads to the development of suppressor cells. This hypothesis is supported by a number of recent studies. DeFabo and Noonan (DeFabo E. C. et al., 1983) have suggested that UV-irradiation of the skin results in the isomerization of urocanic acid (trans to cis) which may play a role in the induction of suppressor cells. Ross, J. A. et al., (1988) subsequently demonstrated the injection of cis-urocanic acid into normal mice could induce antigen-specific suppressor cells. Swartz R. P. (1984) found that when serum from UV-irradiated mice was injected into normal animals, their ability to respond to contact allergens was significantly depressed. Experiments by Robertson et al. (1987) demonstrated that the intravenous injection of IL-1 could mimic the effect of UV and cause suppression of CHS. This effect was overcome by indomethacin, suggesting a possible role for prostaglandins. Since IL-1 is released into the serum of mice after UV irradiation, Gahring et al. (1984) suggested that the severe phototoxicity resulting from UV exposure may cause the release of IL-1 into the circulation and be responsible for the down regulation of CHS. Direct evidence for the release of cytokines from UV-irradiated epidermal cells comes from Schwarz et al. (1986, 1987) who found that in vitro irradiation of epidermal cell cultures caused the release of a soluble mediator into the culture supernatant. Injection of the culture supernatants into mice could mimic the effect of whole-body UV-irradiation and suppress the development of CHS. Furthermore, a 40 kilo-dalton molecule isolated from the suppressive supernatant inhibited the ability of IL-1 to stimulate thymocyte proliferation. The addition of indomethacin to the epidermal cell cultures did not affect the generation of the suppressive supernatant, suggesting a different mechanism from that described by Robertson et al. (1987).

A question that is addressed in this Example is: can the injection of supernatants from UV-irradiated keratinocytes followed by alloantigenic sensitization induce alloantigen-specific Ts? The data demonstrate here that a soluble product from UV-irradiated keratinocytes can mimic the effect of total body exposure to UV radiation and suppress DTH and MLR to alloantigen. Antigen-specific suppressor T cells are found in the spleens of the animals injected with the supernatants from the UV-irradiated keratinocytes. These data suggest the suppressive cytokines released from UV-irradiated keratinocytes may play a role in the induction of antigen-specific suppressor T cells after exposure to UV radiation. Furthermore, these data suggest that the use of factors released from UV-irradiated keratinocytes should provide a novel approach of suppressing the rejection of organ transplants.

Materials and Methods for Example 10

Animals

Specific-pathogen-free female C3H/HeN, BALB/c, and C57B1/6 mice were obtained from the Animal Production Area, Frederick Cancer Research Facility, Frederick, Md. The animals were housed and cared for according to the guide for the care and use of laboratory animals (DHHS publication # (NIH) 78-23), and their use was approved by the institutional animal care and use committee.

Exposure of Mice to UV Radiation

The method used has been described in detail elsewhere (Ullrich S. E., 1986). The dorsal skin of the mice was shaved and the animals were exposed to UVB (280 nm–320 nm) radiation provided by a bank of six FS-40 sunlamps (Westinghouse, Bloomfield, N.J.). The total dose received by the mice during a 3 hr exposure was 40 kJ/m$^2$.

In vitro UV-Irradiation of Epidermal Cell Cultures

The procedure of Schwarz et al. (1986) was used to irradiate epidermal cell cultures. Five million Pam 212 cells (kindly provided to us by Dr. Stuart Yuspa, National Cancer Institute) were added to 100 mm tissue culture dishes in minimum essential medium (MEM) supplemented with 10% fetal calf serum and cultured overnight. The medium was removed and the cells were resuspended with phosphate-buffered saline (PBS). The monolayers were then exposed to 200 J/m$^2$ of UVB radiation. The source of the radiation was a single FS-40 sunlight bulb (Westinghouse, Bloomfield, N.J.), with an output of 1.43 W/m$^2$, at a tube to target distance of 20 cm. After irradiation the cells were washed 3 times with PBS and resuspended in serum-free MEM. Twenty-four hours later the supernatants were removed and passed through a 0.2 micron filter. The protein concentration was determined by the Bradford assay (Bio-Rad, Rockville Centre, N.Y.). Approximately 5 to 10 micrograms of protein was injected into each mouse. Control supernatants were obtained from Pam 212 cells handled in a similar manner but not exposed to UV radiation. Endotoxin contamination was below the limit of detection (0.125 ng/ml) as determined by the Limulus amebocyte lysate assay (Cape Cod Associates, Woods Hole, Mass.).

Effect of Supernatants from UV-Irradiated Epidermal Cells on DTH to Alloantigens C3H or BALB/c mice were injected i.v. with 0.5 ml of the supernatants from UV-irradiated Pam 212 cells or with 0.5 ml of control supernatants. Five days later the mice were immunized by a subcutaneous injection of 5×10$^7$ allogeneic spleen cells. Six days later the mice were challenged by injecting 10$^7$ allogeneic spleen cells into each hind footpad. The footpad swelling was measured 24-h later with an engineer's micrometer (Swiss Precision Instruments, Los Angeles, Calif.). The background response was calculated from the footpad swelling found in non-immunized mice. The specific footpad swelling was determined by subtracting the background response from the response found in the immunized mice.

Adoptive Transfer of Suppressor Cells

Spleens were removed from mice that had a suppressed DTH response. Single-cell suspensions were prepared and 10$^8$ cells were injected into the tail veins of syngeneic recipient mice. Immediately after the cell transfer these mice were immunized with 5×10$^7$ allogeneic spleen cells. Six days later the mice were challenged as described above. The immune response to the allogeneic spleen cells was determined by measuring the animal's footpad swelling 24 hours later.

Effect of Supernatants from UV-Irradiated cells on the Mixed Lymphocyte Response (MLR)

C3H mice were injected i.v. with 0.5 ml (5 to 10 micrograms of protein) of supernatants from the UV-irradiated Pam 212 cells. Five days later the mice were immunized by a subcutaneous injection of 5×10$^7$ B6 spleen cells and, seven days later, their spleens were removed and single-cell suspensions prepared. The responder cells were resuspended in RPMI medium (Ullrich and Kripke, 1984), and $2 \times 10^5$ responder cells were mixed with an equal number of gamma-irradiated (5000 rads) B6 stimulator cells and cultured for 5 days in a 96-well round-bottomed microtiter plate. During the last 18 hours of culture, 1 micro-Ci of tritiated thymidine (ICN Radiochemicals, Irvine, Calif.) was added to each well. The incorporation of the radioisotope into newly synthesized DNA was determined by harvesting the cells with an automated sample harvester and by liquid scintillation counting.

Removal of T cells

In certain experiments T lymphocytes and T cell subsets were depleted by the use of monoclonal antibodies and complement as described previously (Ullrich, S. E. and M. Magee, 1988).

Effect of Indomethacin and Cycloheximide on the Generation of the Suppressive Supernatants Pam 212 cells were treated with UV radiation as described above. Immediately after exposure, 10 micrograms/ml of indomethacin or 10 micrograms/ml of cycloheximide was added to the cultures (Sigma Chemical Co., St. Louis, Mo.). 24 hr later the supernatants were collected and the low molecular weight inhibitors were removed by dialysis against PBS (Spectrophore dialysis tubing, 6–8000 molecular weight cut off, Fisher Scientific, Houston, Tex.). The supernatants were injected i.v. into C3H mice that were sensitized with BALB/c spleen cells as described above. A one way MLR against allogeneic spleen cells was set up 7 days later as described previously.

Lectin Affinity Columns

Supernatants from the UV-irradiated or control keratinocytes (100 μg total protein) were added to Con A bound to agarose (0.5 ml packed gel, Sigma Chemical Co.). The supernatants and the Con A-agarose were mixed together at 4° for 30 minutes, and then added to a 1 ml syringe. The unbound material was eluted with 5 ml of PBS. The bound material was eluted by adding 5 ml of 1 M-α-methyl-D-glucoside followed by 5 ml of 1M α-methyl-D-mannoside. Both the unbound and bound materials were concentrated by ultrafiltration, and 10 μg was injected into C3H mice. Five days later, the animals were sensitized with alloantigen as described above, and the suppression of the MLR was used to indicate which fraction retained the suppressive activity. The fractions from the Con A columns were further analyzed by SDS-PAGE under reducing and non-reducing conditions according to the methods described by Laemmli (Laemmli, U. K. 1970). The proteins were visualized by silver staining (Bio-Rad, Rockville Centre, N.Y.).

IL-1 Bioassay

Il-1 activity was measured by the proliferation of the IL-1 dependent murine helper cell line D10.G4.1.1 as described (Gottlieb et al., 1989). The cells ($10^4$ per well) were added to a 96-well microtiter dish in medium containing 2.5 μg/ml of Con-A (Sigma Chemical Co. St. Louis, Mo.) together with various dilutions of the supernatants from the UV-irradiated or control keratinocytes. In addition, various amounts of murine rIL-1 (Genzyme Corp. Boston, Mass.) was used to generate a standard curve. After a 48 hour culture period, 1 μCi/well of tritiated thymidine was added and 24 hours later the cells were harvested on glass fiber filters and the radioactivity incorporated was measured as described above.

Statistical Analysis

The two tailed Student's t-test was used to determine statistically significant differences between experimental and control groups. In experiments in which DTH was used as a measure of immune responsiveness, there were 5 mice per group. In experiments in which the MLR response was measured there were generally 2–3 mice per group. The response of each individual animal was measured and the data pooled. Each experiment was repeated at least twice.

RESULTS

Effect of supernatants from UV-irradiated keratinocytes on the immune response to alloantigens. Previous reports from this laboratory demonstrated that exposure of mice to UV radiation prior to immunization suppressed the induction of DTH to alloantigen (Ullrich S. E., 1986) (Ullrich, S. E. et al., 1988) The injection of supernatants from UV-irradiated keratinocytes was studied to determine if it could mimic the effect of total-body UV irradiation and suppress DTH. Mice were injected with the suppressive supernatants or exposed to 40 $kJ/m^2$ of UV radiation. Control mice were shaved but not irradiated or injected with supernatants from non-irradiated Pam 212 cells. Five days later the mice were sensitized with alloantigen. DTH to the alloantigen was then measured 7 days later. The data presented in Table 7 demonstrate that mice injected with supernatants from UV-irradiated epidermal cells exhibit little or no response against allogeneic cells.

TABLE 7

EFFECT OF SUPERNATANTS FROM UV-IRRADIATED KERATINOCYTES ON DTH

| Treatment[a] | | footpad[b] thickness | Specific footpad swelling | %[c] suppression | P<[d] |
|---|---|---|---|---|---|
| Exp. 1 | NONE | 2 ± 3 | 0 | | |
| | NR | 42 ± 7 | 40 | 0 | |
| | UV | 19 + 11 | 17 | 58 | .001 |
| | Pam SN | 32 ± 9 | 30 | 25 | NS |
| | UV-Pam SN | 19 ± 4 | 17 | 58 | .001 |
| Exp. 2 | NONE | 13 + 5 | 0 | | |
| | NR | 41 ± 6 | 28 | — | |
| | UV | 26 ± 4 | 13 | 54 | 0.001 |
| | UV-L929SN | 33 ± 6 | 20 | 29 | NS |
| | UV-J774.1SN | 35 ± 4 | 22 | 21 | NS |
| Exp. 3 | NONE | 3 ± 3 | 0 | | |
| | NR | 21 ± 3 | 18 | 0 | |
| | UV | 9 ± 5 | 6 | 67 | .001 |
| | Pam SN | 29 ± 6 | 26 | 0 | NS |
| | UV-Pam SN | 4 ± 4 | 1 | 95 | .002 |

[a]Mice were injected i.v. with SN from UV-irradiated Pam 212 cells (UV-SN), SN from non-irradiated control cells (PAM-SN) or exposed to 40 $kJ/m^2$ UV radiation. In experiment 1 and 2, C3H mice were sensitized with BALB/c spleen cells. In Experiment 3, BALB/c mice were sensitized with C3H spleen cells. There were 5 mice per group.
[b]Units: cm × $10^{-3}$;
[c]% suppression = [1 − (specific footpad swelling experimental/specific footpad swelling control)] × 100.
[d]P values determined by two-tailed Student's t-test, experimental vs. NR (non-irradiated control mice); NS = P > .01.

The response observed in mice previously exposed to UV was significantly less than that observed in the non-irradiated control mice (NR). Similarly, the response seen in mice injected with supernatants from the UV-irradiated Pam 212 cells was significantly suppressed, whereas, the injection of supernatants from the non-irradiated Pam 212 cells did not cause a significant suppression of DTH. It should be noted that the Pam 212 cell line is of BALB/c origin. Because the intravenous introduction of foreign histocompatibility antigens can suppress DTH (37) it is possible that the suppression observed in Experiment 1 was an artifact resulting from the release of H-2 antigens into the supernatant by the UV-irradiated Pam 212 cells. To rule out this possibility, supernatants from UV-irradiated Pam 212 cells were injected into BALB/c mice (Experiment 3, Table 7). These mice were then immunized with C3H spleen cells. The DTH response of BALB/c mice to C3H antigens was also suppressed, suggesting that the effect could not be attributed to the release of alloantigens into the medium by the irradiated Pam 212 cells. These data also indicate that the induction of suppression by the supernatants is not H-2 restricted.

The presence of suppressor cells in the spleens of mice in which the DTH response was depressed was investigated. As shown in Table 8, transfer of spleen cells from mice injected with supernatants from the UV-irradiated Pam 212 cells (UV Pam 212 SN) could inhibit the induction of DTH in normal recipient animals.

TABLE 8

ANTIGEN-SPECIFIC SUPPRESSOR CELLS ARE PRESENT IN THE SPLEENS OF MICE INJECTED WITH SUPERNATANTS FROM UV-IRRADIATED KERATINOCYTES

| Source of[a] donor cells | Sensitizing antigen suppression | footpad[b] thickness | specific swelling[b] | %[b] |
|---|---|---|---|---|
| none | none | 14 ± 5 | 0 | |
| none | BALB/c | 57 ± 13 | 43 | — |
| Pam 212 SN | BALB/c | 57 ± 13 | 43 | 0 |
| UV Pam 212 SN | BALB/c | 35 ± 5*[c] | 21 | 51 |
| none | none | 17 ± 5 | 0 | |
| none | B6 | 32 ± 7 | 15 | — |
| Pam 212 SN | B6 | 38 ± 8 | 21 | 0 |
| UV Pam 212 SN | B6 | 36 ± 7 | 19 | 0 |

[a]Donor mice were injected with from supernatants (10 micrograins of protein) from the non-irradiated control Pam 212 cells or the UV-irradiated keratinocytes. 5 days later all the donor mice were injected with 5 × 10$^7$ BALB/c spleen cells. DTH of the donor mice was read 7 days after sensitization and 1 × 10$^8$ donor spleen cells were transferred into two groups of recipient mice. One group was sensitized with BALB/c spleen cells, the second withB6 spleen cells; DTH of the recipient mice against the sensitizing antigen was read 7 days later. The background response was measured in mice that were not sensitized but were challenged with the antigen.
[b]See footnotes for Table 7.
[c]*P < 0.001 two tailed Student's t-test vs the control.

The injection of spleen cells from mice injected with control supernatants (Pam 212 SN) did not significantly suppress the recipient animals' immune response. The specificity of the suppression was also examined. Spleen cells from C3H mice, injected with the supernatants from the UV-irradiated keratinocytes and sensitized with BALB/c cells, were transferred into normal C3H mice. The recipients were then sensitized and challenged with B6 spleen cells. While the transfer of suppressor cells from mice injected with the suppressive supernatants and sensitized with BALB/c cells did suppress DTH when the recipients were sensitized with BALB/c cells, these cells had no effect on the magnitude of the DTH response against B6, indicating the specificity of the suppressor cells.

The effect of injecting supernatants from the UV-irradiated keratinocytes on the ability of spleen cells from treated mice to generate a MLR was also examined. C3H mice were injected with supernatant from the UV-irradiated keratinocytes (10 micrograms of protein) or exposed to UV radiation. Five days later all the mice were injected with B6 spleen cells. This was done because a previous study had demonstrated that in order to suppress the MLR, mice must be first exposed to UV radiation and then sensitized with the alloantigen. Exposure to UV radiation alone will not induce suppression (Ullrich, 1986). Seven days later, spleen cells from these mice were used as responder cells in the MLR. As shown in Table 9, spleen cells from mice injected with the supernatants from the UV-irradiated keratinocytes do not proliferate in response to the alloantigen.

TABLE 9

INABILITY OF SPLEEN CELLS FROM MICE INJECTED WITH THE SUPERNATANT FROM UV-IRRADIATED KERATINOCYTES TO PROLIFERATE TO ALLOANTIGEN

| | γCPM | | | |
|---|---|---|---|---|
| | Experiment 1 | | Experiment 2 | |
| Treatment | 3 day | 5 day | 3 day | 5 day |
| NR | 62994 ± 4008 | 30633 ± 1312 | 60182 ± 9571 | 42489 ± 5633 |
| UR | 6952 ± 1738* | 7049 ± 736* | 32026 ± 3856* | 13206 ± 4472* |
| Pam 212 SN | 55113 ± 6304 | 43255 ± 4403 | 59490 ± 5894 | 37804 ± 2361 |
| UV Pam 212 SN | 7236 ± 2395* | 6219 ± 1395* | 31056 ± 4915* | 22175 ± 2654* |

[a]Spleen cells were obtained from the non-irradiated controls (NR), mice exposed to 46 kJ/m$^2$ of UV radiation (UV), mice injected with supernatants from the non-irradiated control cultures (Pam SN), or mice injected with supernatants (10 μg protein) from the UV-irradiated keratinocytes (UV Pam SN). All mice were sensitized with alloantigen 5 days after UV exposure or injection of the keratinocyte-derived supernatants. Cells were culturedwith gamma-irradiated allogeneic stimulator cells for 3 or 5 days. Data is expressed as Δ CPM; the background response of the responder cells cultured alone was subtracted.
*P < 0.001, two-tailed Student's t-test vs. the NR control.

Compared to the response seen in the control (normal mice immunized with alloantigen, NR), exposure of mice to UV radiation prior to sensitization, or injecting the supernatant from the UV-irradiated keratinocytes, caused a significant depression of the proliferative response. The injection of the supernatant from the non-irradiated keratinocytes had no suppressive effect (P>0.05). Note that the cells were harvested after 3 or 5 days of culture. Regardless of duration of the culture period, exposure of mice to UV radiation or injecting the supernatant from the UV-irradiated keratinocytes, resulted in a significant suppression (P<0.001) of the proliferative response. Thus a simple shift in the kinetics of the response does not explain the observed suppression of proliferation. The enhanced response of the 3 day cultures can be explained by the fact that the cells were isolated from mice that were injected with alloantigen. Since however, normal cells do not proliferate to alloantigen after a 3-day culture (data not shown) we have chosen to use the 5 day culture period in all further experiments so that the specificity of the suppression can be measured.

To examine the specificity of the suppression, spleen cells were obtained from mice injected with the suppressive supernatants and sensitized with B6 cells. As before, when these cells were cultured with gamma-irradiated B6 stimulator cells there was little to no proliferation (Table 10).

TABLE 10

SPECIFICITY OF THE SUPPRESSION INDUCED BY INJECTING
SUPERNATANTS FROM UV-IRRADIATED KERATINOCYTES

| | | CPM ± SEM | |
|---|---|---|---|
| Treatment of mice[a] | cells alone | cells + B6 | cells + BALB/c |
| Exp. 1 Medium + B6 cells | 3188 ± 667 | 31592 ± 2519 | 33382 ± 1149 |
| Pam. 212 SN + B6 cells | 4250 ± 134 | 30157 ± 1325 | 32065 ± 2330 |
| UV Pam 212 SN + B6 cells | 4428 ± 687 | 15550 ± 3883* | 35622 ± 283 |
| Exp. 2 Medium + B6 cells | 862 ± 372 | 53780 ± 9676 | 39416 ± 5700 |
| Pam 212 SN + B6 cells | 2960 ± 832 | 61428 ± 7100 | 70764 ± 6515 |
| UV Pam 212 SN + B6 cells | 2749 ± 450 | 25472 ± 4428* | 37448 ± 5724 |
| Medium + BALB/c cells | 940 ± 388 | 32576 ± 6656 | 57138 ± 8292 |
| Pam 212 SN + BALB/c cells | 3720 ± 2068 | 45196 ± 5330 | 50732 ± 8988 |
| UV Pam 212 SN + BALB/c cells | 2740 ± 576 | 53526 ± 4060 | 20052 ± 3224* |

[a]Mice were injected with supernatants from the UV-irradiated keratinocytes (UV Pam 212 SN) or supernatants from the control cells (Pam 212 SN) and then sensitized with B6 or BALB/c spleen cells. The proliferative response of their spleen cells was compared to the response of the normal control spleen cells.
*P < 0.001 two-tailed Student's T-test.

When the same cells were cultured with BALB/c stimulator cells rather than B6 stimulator cells, they generated a MLR that was indistinguishable from that of the normal control cells (Exp. 2). These findings demonstrate that like the suppression induced by exposure of mice to UV, the suppression induced by injecting supernatants from UV-irradiated Pam 212 cells was specific for the antigen subsequently used to sensitize the animal.

Figure 6:
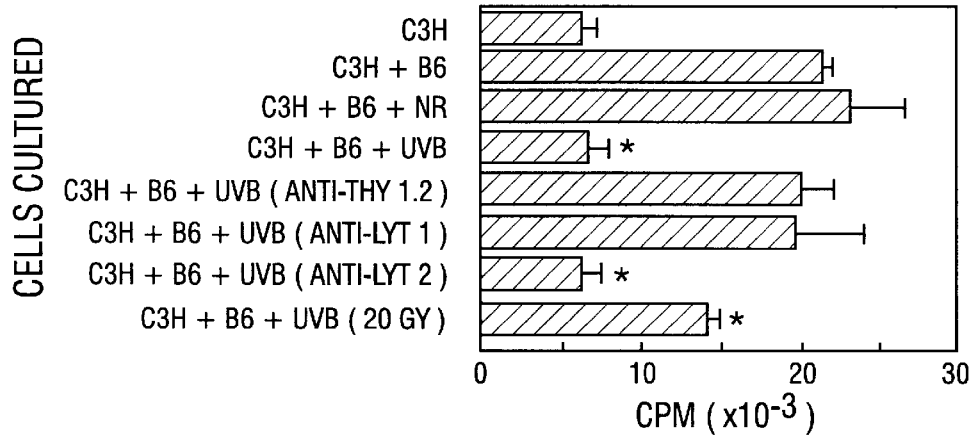
FIG. 6 shows the phenotype of the suppressor cells induced by injecting supernatants from UV-irradiated keratinocytes into mice. Spleen cells from mice injected with supernatants from the UV-irradiated keratinocytes where added to one way MLR cultures containing normal C3H responder cells and gamma-irradiated B6 stimulator cells. Spleen cells from the mice injected with the suppressive cytokines were treated with various monoclonal antibodies and complement. One group of cells was exposed to 2000 rad of gamma radiation. Control cells (UV and NR) were treated with complement. * indicates a significant difference from the proliferation of the control; P<0.001.

To determine whether T-cells were responsible for suppressing the MLR, spleen cells from C3H mice, injected with the suppressive supernatants and sensitized with B6 were treated with anti-Thy 1.2 monoclonal antibody and complement. The remaining cells were added to cultures of normal C3H spleen cells and gamma-irradiated BALB/c stimulator cells. The data from this experiment shown in FIG. 6, demonstrate that Ts are generated in the spleens of mice injected with supernatants from the UV-irradiated Pam 212 cells. Whereas the addition of complement treated cells (C3H+B6+UV) caused a significant suppression of the MLR (P<0.001) compared to the control, C3H+B6), the depletion of T lymphocytes totally abrogated the suppressive effect. In addition, depletion of the Lyt 1+ subset of T cells also caused a total abrogation of suppression. Depletion of the Lyt 2+ cells had no effect on the suppression of the MLR. Irradiation of the suppressor cells with 20 Gy of gamma radiation reduced the suppressive effect to a degree, however there was still a significant difference from the control (P<0.001). As for the specificity of the suppression, the addition of spleen cells from mice initially injected with the suppressive supernatants and sensitized with B6 cells had no suppressive effect when BALB/c spleen cells were used as stimulators (34528±4868 CPM, C3H+B6) compared with (31983±4524 (PM, C3H+B6 UVB) when supernatants from the UV-irradiated Pam 212 cells were injected). Thus, a Thy 1+Lyt 1+, 2−, radiation resistant, antigen-specific suppressor cell is induced after injecting the supernatants from the UV-irradiated keratinocytes into mice.

Figure 7A:
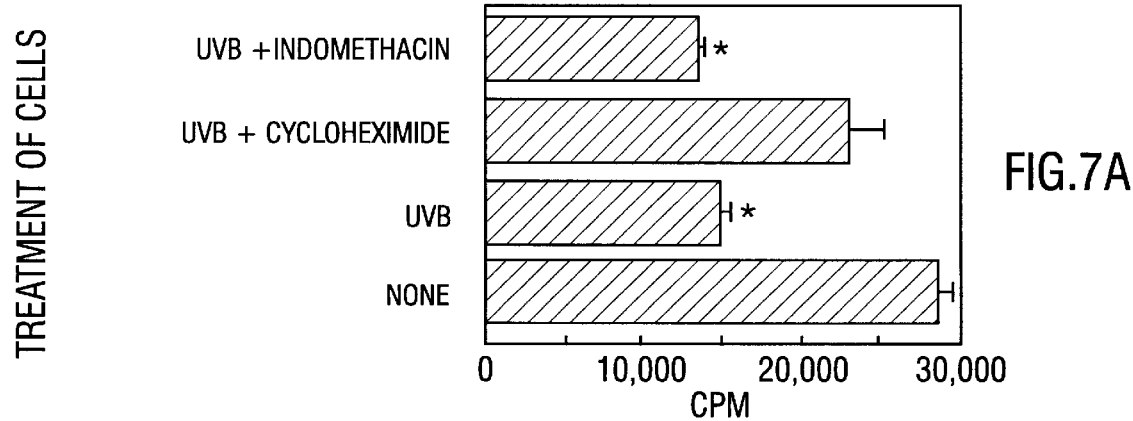
FIG. 7A and FIG. 7B shows physical properties of the suppressive cytokine released from UV-irradiated keratinocytes. In panel A Pam 212 cells were exposed to 200 J/m$^2$ of UV radiation and then treated with 10 micrograms/ml of indomethacin or 10 microgram/ml of cycloheximide. Supernatants from the treated cells and the control cultures (UV and NR) were dialyzed and then injected into mice. In panel B the supernatants were harvested and then treated with heat or trypsin (10 microgram/ml). The treated supernatants were then injected into mice and the resulting MLR was measured. The background response of responder cells cultured alone was 4290±960 CPM. * indicates a significant difference from the control; P<0.001.
Figure 7B:
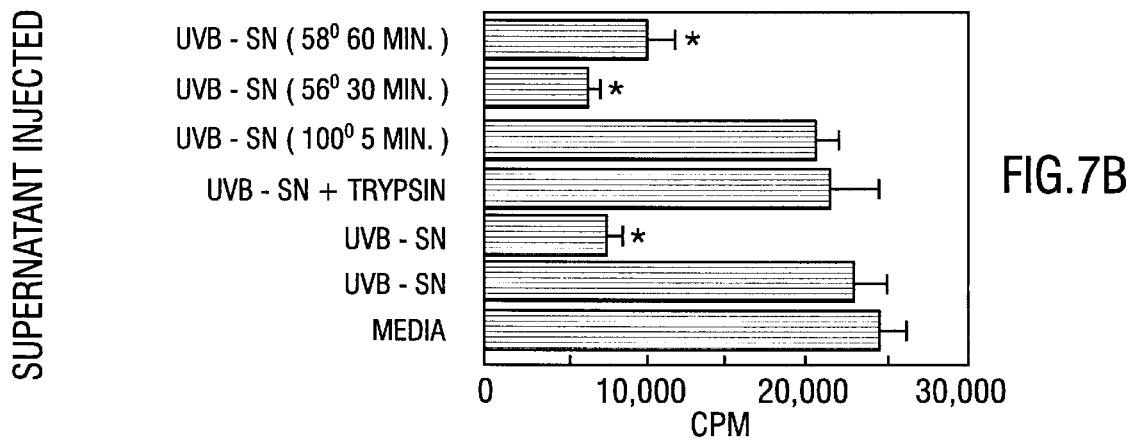

Certain characteristics of the suppressive material are shown in FIG. 7A and FIG. 7B. In this experiment two approaches were used. In panel A, the Pam 212 cells were exposed to UV and then treated with either the prostaglandin synthetase inhibitor, indomethacin or with cycloheximide, which interferes with protein synthesis. Twenty-four hours later all the supernatants were collected, dialyzed to remove the low molecular weight inhibitors and injected into mice. Note that the inhibition of protein synthesis interferes with the ability of the UV-irradiated cells to generate the suppressive cytokine, while the inhibition of prostaglandin synthesis did not. Dialysis had no effect on the ability of the supernatant from the UV-irradiated keratinocytes to suppress the induction of the MLR. In panel B the supernatants from the UV-irradiated keratinocytes were collected and heated, boiled or treated with 10 micrograms/ml of trypsin. Compared to the controls (mice injected with media or supernatants from the non-irradiated cells) injection of the supernatant from the UV-exposed keratinocytes suppressed the generation of the MLR. Boiling the supernatant or treating it with trypsin totally removed the suppressive effect. Exposure to 56° C. for 30 minutes or 1 hr had no effect on the ability of the supernatant to suppress the MLR. The conclusion from these data is that the suppressive cytokine released from UV-irradiated keratinocytes is a non-prostaglandin like, non-dialysable protein or peptide.

An intriguing and not completely answered question about the suppression induced by such UV radiation is; how does exposure of the dorsal skin of mice to UV radiation result in a systemic suppression of the immune response, one that is characterized by the appearance of splenic antigen-specific suppressor T cells? Clearly, the UV radiation is not penetrating to the spleen (Evertt, M. A. et al., 1966), so direct irradiation of the T cells of the spleen is not possible. Because the limited penetration of UV radiation confines its primary effect mainly to the skin, the release of soluble suppressive factors by UV-treated epidermal cells is an attractive hypothesis to explain the systemic suppression of the immune response by UV radiation. The present invention relates to using such a suppressive factor to suppress, in an antigen-specific manner, the immune response to an antigen. The ability of cytokines from UV-irradiated keratinocytes to induce antigen specific suppressor T cells was tested as described herein. These data demonstrate the following: (1) DTH to antigens can be suppressed by the factor released from UVB-irradiated keratinocytes; (2) the suppressive activity of the factor is not H-2 restricted; (3) suppressor cells are induced; (4) the suppressor cells are specific for the antigen used to sensitize the mice injected with the suppressive cytokine; and (5) the suppressor cells are T cells. Since the immunosuppression induced by the injection of this factor is very similar to that seen after exposure of mice to UV radiation (Ullrich S. E., 1986, Ullrich, S. E., 1988) these findings support the hypothesis that the systemic suppression of DTH in vivo following UVB-irradiation is the result of the release of suppressive cytokines by UVB-irradiated keratinocytes. The identity of one such cytokine is herein identified as an immunosuppressive factor reactive with an antibody directed toward IL-10, in particular, the cytokine is IL-10.

Dose of supernatants from UV-irradiated keratinocytes required to induce suppression.

Figure 8:
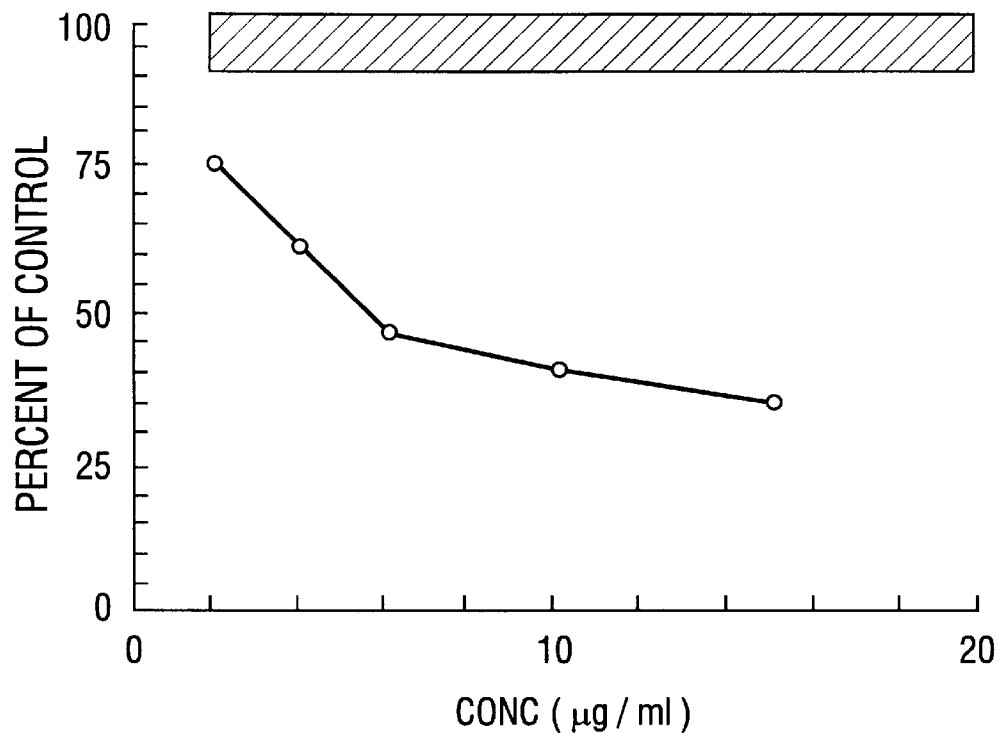
FIG. 8 shows dose-response curve for suppressing the MLR. Various concentrations of culture supernatants from the UV-irradiated keratinocytes were injected into mice and the ability of their spleen cells to proliferate in response to alloantigen was measured. The data are expressed as a percentage of the control response (mice injected with media; 34,456±2215 cpm is equal to 100%; the background response was 3,072±495 cpm). The cross-hatched region represents the proliferation of spleen cells from mice injected with supernatants from non-irradiated keratinocytes.
Figure 9:
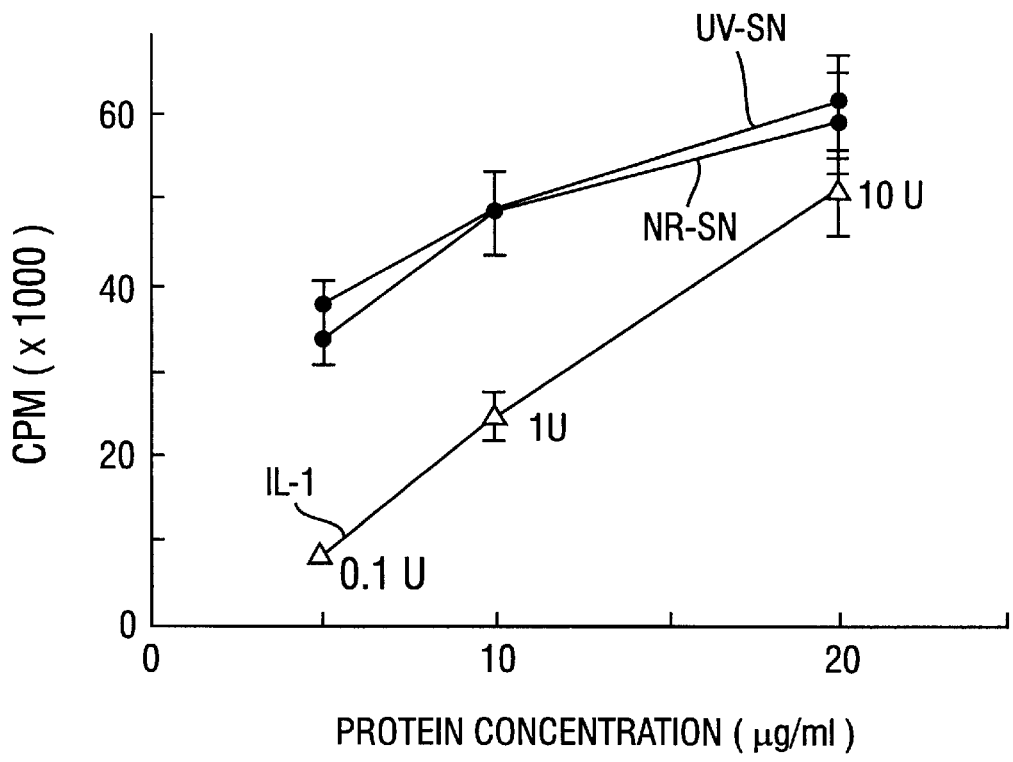
FIG. 9 shows production of IL-1 by the UV-irradiated and control keratinocytes. Supernatants were obtained from the UV-irradiated or control nonirradiated Pam 212 cells. Protein concentration was measured and various concentrations were added to the IL-1 dependent D10.G4.1 helper cell line. A standard curve was generated by adding dilutions of murine rIL-1 to the cells.

The dose-response curve for the suppression of the MLR is shown in FIG. 8. C3H mice were injected with various concentrations of supernatants from the UV-irradiated and non-irradiated keratinocytes and 5 days later were sensitized with B6 cells. One week later their spleens were removed, and the proliferation in response to alloantigen was measured. The control response (34,456 cpm=100%) was determined by measuring the proliferation of spleen cells isolated from mice injected with medium and immunized with alloantigen. Although injecting supernatants from the non-irradiated cells had no suppressive effect, injecting increasing amounts of supernatants from the UV-irradiated keratinocytes increased the degree of suppression. From these data, the present inventors determined that the amount of suppressive material needed to cause a 50% suppression of the response was between 7 and 10 µg of protein. Therefore, in all subsequent experiments at least 10 µg of protein was injected.

Measurement of IL-1 present in the supernatants from the UV-irradiated keratinocyte cultures.

Pam 212 constitutively produce IL-1. Because data published by Robertson et al. (1987) indicated that the iv injection of IL-1 can suppress the induction of a contact hypersensitivity reaction and since UV exposure has been shown to modulate the expression of IL-1 mRNA, and the release of IL-1 by keratinocytes (Ansel et al., 1988; Luger et al., 1989) it is possible that the overproduction of IL-1 by our UV-irradiated Pam 212 cells may be responsible for the suppression we see. To address this question we measured the amount of IL-1 released into the medium after exposure of the keratinocytes to UV radiation. The keratinocytes were exposed to UV radiation as described and 18 hours later the supernatants collected and added to the IL-1 dependent, D10.G4.1, T helper cell line. Control supernatants were obtained from keratinocytes treated in an identical manner but not exposed to UV radiation. As can be seen from the data presented in FIG. 8, exposing the Pam 212 cells to 200 J/m$^2$ of UV radiation did not cause a significant increase in the release of IL-1. The proliferation of the D10.G4.1 cells cultured with the supernatant from the UV-irradiated Pam 212 cells was identical to that seen when supernatants from the non-irradiated control keratinocytes were used. Because injecting the supernatants from the control non-irradiated keratinocytes cells did not suppress the induction of an immune response, whereas injecting supernatant from the UV-irradiated cells did, we conclude that the release of IL-1 by the keratinocytes is not responsible for the observed suppression.

Binding of the suppressive material to Con A-agarose columns.

Supernatants from the UV-irradiated and control non-irradiated keratinocytes were added to agarose beads coupled with Con A (Table 11).

TABLE 11

Fractionation of the suppressive material on lectin affinity columns

| Fraction injected[a] | CPM ± SEM | | ΔCPM | % Suppression |
|---|---|---|---|---|
| | Cells alone | Cells + BALB/c | | |
| Medium | 5417 ± 294 | 46786 ± 3791 | 41369 | — |
| NR SN | 3394 ± 120 | 39657 ± 4853 | 36263 | 12 |
| UV starting material | 7525 ± 383 | 29833 ± 2537*[b] | 22308 | 47 |
| UV unbound | 5217 ± 525 | 39449 ± 5093 | 34232 | 17 |
| UV glucoside eluate | 5527 ± 850 | 48739 ± 5774 | 43212 | 0 |
| UV mannoside eluate | 5208 ± 1013 | 28815 ± 520*[b] | 23607 | 43 |
| NR unbound | 6232 ± 192 | 46574 ± 7029 | 40342 | 2 |
| NR glucoside eluate | 3122 ± 1643 | 42986 ± 6259 | 39864 | 4 |
| NR mannoside eluate | 4775 ± 981 | 38035 ± 954 | 33260 | 20 |

[a]Supernatants (100 µg of protein) from the control non-irradiated (NR) keratinocytes and the UV-irradiated keratinocytes (UV) were mixed with Con A agarose (0.5 ml packed gel) and incubated at 4° for 30 minutes. The gel was added to 1.0 ml syringes, and 5 ml of PBS was added to elute the unbound material. the bound material was eluted by the addition of 5 ml of 1 M α-methyl-D-glucoside followed by 5 ml of 1 M α-methyl-D-mannoside. The elutedfractions were dialyzed against PBS, concentrated by ultrafiltration, and 10 µg of protein was injected into C3H mice. The mice were sensitized with alloantigen. The MLR was measured as described in Materials and Methods.
[b]*P < 0.001, Student's two-tailed t-test vs. medium control.

As seen in Table 11, the flow-through material (UV unbound) had little suppressive activity when compared with that of the starting material (UV SN), indicating that the majority of the suppressive material bound to the Con A. Because both α-D-glucosyl and α-D-mannosyl residues bind to Con A, an attempt was made to elute the bound material by competition with excess amounts of α-methyl-D-glucoside and α-methyl-D-mannoside. The suppressive activity was found in the fraction eluted with the mannoside (UV mannoside eluate) but not with the glucoside (UV glucoside eluate). No significant suppression was noted when the control supernatants was fractionated on the Con A-agarose columns (NR mannoside eluate, NR glucoside eluate).

Because the ability of the supernatants from both the UV-irradiated cells and the control non-irradiated cells to support the proliferation of the IL-1-dependent cell line, D10.G4.1 is equivalent it does not appear that the overproduction of IL-1 by the UV-irradiated keratinocytes is responsible for the suppression we describe. The suppressive factor described here binds to concanavalin-A agarose columns, indicating that it is a glycoprotein, whereas IL-1 is not glycosylated, further indicating that the suppression of DTH observed after injecting the supernatants from the UV-irradiated keratinocytes was not due to the injection of IL-1.

There are several similarities between the immunosuppression induced by UV radiation and that induced by thermal injury. The presence of I-J+Lyt 1+2– Ts cells in the spleens of mice early after thermal trauma (Kupper, T. et al., 1984) and the presence of similar cells in the spleens of mice following UV irradiation and antigenic sensitization (Ullrich, S. E., 1988) may lead to speculation that a similar mechanism is involved in their induction. Perhaps the release of soluble products from damaged epidermal cells is involved in the induction of suppressor cells in both these systems.

A major goal of transplantation biology is to suppress, in an antigen-specific manner, the response of the host against a foreign graft. Perhaps the most significant aspect about the data presented herein is the ability to use supernatants from UV-irradiated keratinocytes or analogous preparations with the 68 kDa glycoprotein to suppress, in an antigen-specific manner, the immune response to alloantigen. It may be possible therefore to use this factor to induce antigen-specific suppressor cells and suppress the rejection of foreign tissue grafts. Thus, the injection of suppressive cytokines from UV-irradiated keratinocytes should provide a novel method of inducing a specific suppression of allograft rejection.

EXAMPLE 11

Effect of UV-Irradiation of Keratinocytes on IL-10 mRNA Expression and IL-10 Secretion into the Supernatant This example describes the effect of UV irradiation of keratinocytes on IL-10 MRNA expression and IL-10 secretion into the supernatant.

MATERIALS AND METHODS

Animals. Specific pathogen-free female C3H/HeNCr (MTV−) and BALB/c AnNCr mice (8–12 weeks old) were purchased from the NCI-Frederick Cancer Research Facility Animal Production Area (Frederick, Md.). Animals are maintained in facilities approved by the American Association for Accreditation of Laboratory Animal Care and in accordance with current United States Department of Agriculture, Department of Health and Human Services, and National Institutes of Health regulations and standards. All animal procedures were approved by the Institutional Animal Care and Use Committee. Within a single experiment all mice were age- and sex-matched. The mice received NIH-31 open formula mouse chow and sterile water ad libitum. Ambient light was controlled to provide regular cycles of 12 h of light and 12 h of dark.

Radiation Sources. A bank of 6 FS-40 sunlamps (Westinghouse, Bloomfield, N.J.) was used to treat mice with UV radiation. These lamps emit a continuous spectrum from 270–390 nm, with a peak emission at 313 nm; approximately 65% of the radiation emitted by these lamps is within the UVB range (280–320 nm). The irradiance of the source averaged 10 $J/m^2/s$, as measured by an IL-700 radiometer, using a SEE 240 UVB detector equipped with A127 quartz diffuser (International Light, Inc., Newburyport, Mass.). Because of shielding by the cage lids, the incident dose received by the animals was approximately 4.5 $J/m^2/s$. The total dose of UVB received was approximately 15 $kJ/m^2$. Prior to irradiation the dorsal hair of the mice was removed with electric clippers. Keratinocyte cultures were irradiated with a single FS-40 bulb. The output of this lamp was 1.43 $J/m^2/s$, at a tube-to-target distance of 23 cm.

Cell lines, Antibodies, and Reagents. The spontaneous transformed murine keratinocyte cell line, Pam 212, was provided by Dr. Stuart Yuspa, National Cancer Institute, Bethesda, Md. (Yuspa, S. H., et al., 1980). HDK-1, a KLH-specific Th1 clone (Cherwinski, H., et al., 1987), and SXC-1, a hybridoma producing rat anti-mouse-IL-10 (IgM isotype) (Mosmann, T. R., et al., 1990), were kindly provided by Dr. Timothy Mosmann, University of Alberta, Edmonton, Canada. D10.G4.1, a conalbumin-specific Th2 clone, was purchased from ATCC (Rockville, Md.). Tissue culture medium and supplements were purchased from GIBCO (Grand Island, N.Y.). Fetal calf serum was purchased from Hyclone Laboratories Inc. (Logan, Utah).

In Vitro UV Irradiation of Keratinocytes. Five million keratinocytes were added to 100-mm tissue culture dishes in 5 ml of MEM supplemented with 10% FCS and cultured overnight. The medium was removed and the keratinocyte monolayers were washed three times with PBS and overlaid with PBS. The monolayers were then exposed to 200 $J/m^2$ of UV radiation. After irradiation, the cells were resuspended in serum-free MEM. Twenty-four hours later, the supernatant fluid was removed. The protein concentration was determined by the Bradford assay (Bio-Rad, Rockville Centre, N.Y.). Approximately 15 to 20 µg of protein was injected into each mouse. Control supernatants were obtained from Pam 212 cells handled in a similar manner but not exposed to UV radiation (mock-irradiated cells). Endotoxin contamination was below the limit of detection (0.125 ng/ml) as determined by the Limulus amebocyte lysate assay (Cape Cod Associates, Woods Hole, Mass.).

Effect of Supernatants from UV-Irradiated Keratinocytes on DTH to Alloantigens. BALB/c mice were injected intravenously with 15–20 µg of supernatant protein from UV-irradiated or mock-irradiated keratinocytes. Five days later, the mice were immunized by a subcutaneous injection of $5 \times 10^7$ allogeneic C3H/HeN spleen cells. Six days later, the mice were challenged by injecting $10^7$ C3H spleen cells into each hind footpad. To assess DTH, footpad swelling was measured 24 h later with an engineer's micrometer (Swiss Precision Instruments, Los Angeles, Calif.). The background response was determined by measuring the footpad swelling of non-immunized mice. The specific footpad swelling was calculated by subtracting the background response from the response found in the immunized mice.

Northern Blot Analysis. Message RNA was isolated using a Micro fast track MRNA isolation kit (Invitrogen Corp. San Diego, Calif.), electrophoresed on 1.5% agarose/formaldehyde gels, and blotted onto nitrocellulose filters. Pre-hybridization was carried out at 42°, for 4 h in 5×SSPE, 0.1% SDS, 1×Denhardt's solution, and 25 µg/ml sheared salmon sperm DNA. Synthetic oligonucleotide probes were synthesized using an Applied Biosystems oligonucleotide synthesizer (Foster City, Calif.). The probes were synthesized based on the published nucleotide sequence of murine IL-10 cDNA as described (Moore, K. W., et al., 1990) and corresponded to positions 18–37 (CGGGAAGACAATAACTGCAC) SEQ ID NO:1, 364–384 (CAGGCAGAGAAGCATGGCCC) SEQ ID NO:2, and 573–592 (ACTGCATAGAAGCATACATG) SEQ ID NO: 3. The probes were labeled with $^{32}$-P, and hybridization was carried out at 4°. The membranes were washed, 18 h later under high-stringency conditions (5×SSPE, 65°) and exposed to X-Omat film (Kodak Corp. Rochester, N.Y.). Equivalent RNA loading was determined by stripping the membrane and rehybridization with an oligonucleotide probe specific for a house keeping gene (β-actin, Oncogene Sciences, Manhasset, N.Y.). The size of the mRNA was determined by the use of an RNA ladder (GIBCO, Grand Island, N.Y.).

IL-10 Bioassay. The inhibition of IFN-γ production by antigen-stimulated Th1 cells as described by Florentino et al. (1989) was used to measure IL-10 bioactivity in the supernatants from UV- and mock-irradiated keratinocytes. HDK-1 cells ($5 \times 10^4$/well) and an equal volume (100 µl) of gamma-irradiated (2,500 rads) BALB/c spleen cells ($5 \times 10^5$/well) were mixed together in 96-well microtiter dishes with 100 µg/ml KLH. After a 24-h culture period, the level of IFN-γ in the supernatant was determined by ELISA (Genzyme Corp. Cambridge, Mass.).

Immunoblotting. Five to 10 µg of protein from UV-irradiated or mock-irradiated keratinocytes were resolved by nonreducing SDS-PAGE and transferred to a nitrocellulose filter. The filter was blocked with 3% non-fat dried milk overnight at 4°. The filter was then probed with 10 µg/ml monoclonal rat anti-mouse IL-10 (SXC-1) for 2 h at 37°. The filter was then washed with Tris-buffered saline (50 mM Tris-HCl, pH 7.0) containing tween-20 (0.05%) and incubated with a 1:1000; dilution of $^{125}$I-labeled goat antirat-IgM (Amersham, Arlington Heights, Ill.). The filter was washed extensively in Tris-buffered saline and autoradiographed at -70° with X-Omat film.

Neutralization of IL-10 activity. One hundred micrograms of protein from UV-irradiated or mock-irradiated keratinocytes was precleared with protein A-agarose beads at 37° for 1 h. The material was centrifuged and the supernatant was transferred to a new microcentrifuge tube. The samples were then incubated with 10 µg/ml of rat anti-mouse IL-10 (SXC-I), isotype-matched control Ab (RA3), or normal rat serum overnight at 4°. The samples were then treated with goat anti-rat IgM (IgG isotype) for 90 min at 37°. All samples were then incubated with protein A-agarose beads at 37° for 60 min. The samples were centrifuged and the supernatant was injected into mice.

RESULTS

Figure 10:
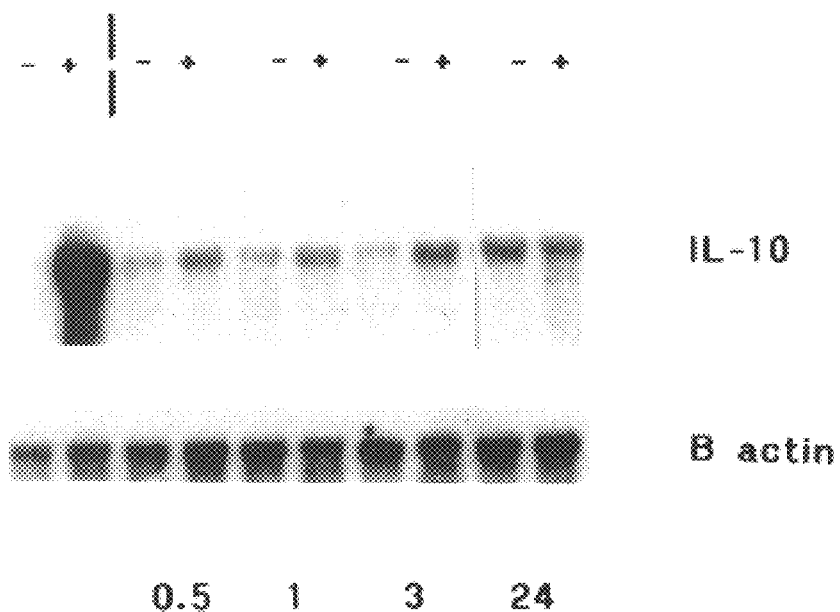
FIG. 10. Up-regulation of IL-10 mRNA expression in UV-irradiated keratinocytes. mRNA was extracted from UV-irradiated (+) or mock-irradiated (−) Pam 212 cells at various times after exposure (30 min, 1, 3, 24 h), separated on 1.5% agarose/formaldehyde gels, blotted onto nitrocellulose filters and analyzed by Northern hybridization with $^{32}$-P-labeled oligonucleotide probes specific for IL-10. As a control for this experiment, mRNA was also extracted from resting (−) and Con A activated (+) D10 cells. Equivalent RNA loading was determined with a probe specific for β-actin.

Effect of UV-Irradiation on IL-10 mRNA expression. To determine whether IL-10 mRNA expression was up-regulated following UV exposure, a Northern blot analysis was performed. Keratinocytes were irradiated with UV, and at various times after exposure mRNA was isolated. As a control for this experiment, mRNA was also isolated from Con A-activated D10.G4.1 cells which secrete IL-10 (Mosmann, T. R., et al., 1990). As can be seen in FIG. 10, exposing keratinocytes to UV radiation enhanced their expression of IL-10 mRNA. At 30 min, 1 h and 3 h after exposure, the expression of IL-10 mRNA is enhanced when compared with the expression seen in the non-irradiated cells. By 24 h there was no difference between the expression observed in the non-irradiated cells versus the irradiated keratinocytes. We are not sure why we see up-regulation of IL-10 mRNA in non-irradiated keratinocytes, but perhaps it reflects a stress reaction by the keratinocytes due to the prolonged serum-free culture conditions. As expected, Con A-stimulated D10.G4.1 cells did express IL-10 mRNA. The size of the keratinocyte-derived IL-10 message was similar (1.4 kilobases) to that described previously by others (Moore, K. W., et al., 1990).

Figure 11:
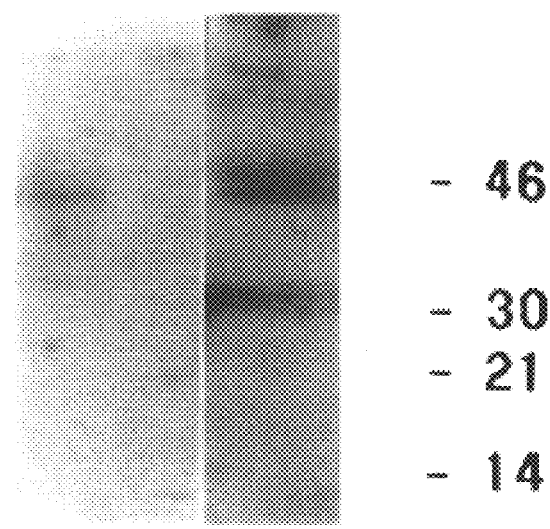
FIG. 11. Monoclonal anti-IL-10 binds to a factor released by UV-irradiated keratinocytes. Supernatants from UV-irradiated keratinocytes (UV), mock-irradiated keratinocytes (NR), or Con A activated D10 cells were separated on 12.5% SDS-PAGE gels, transferred to nitrocellulose membranes, immunoblotted with rat-anti-mouse IL-10 and developed with $^{125}$I-labeled anti-rat IgM.

Secretion of IL-10 by UV-Irradiated Keratinocytes. To determine whether IL-10 was secreted by the UV-irradiated keratinocytes, the present inventors performed a Western analysis. Supernatants from UV-irradiated or non-irradiated cells were resolved on 12.5% SDS-PAGE gels, transferred to nitrocellulose filters, and developed with SXC-1, a rat antimouse IL-10 monoclonal antibody. Immunoreactive IL-10 was found in the supernatants from the UV-irradiated keratinocytes, but no IL-10 was found in the supernatants from the non-irradiated keratinocytes (FIG. 11). As a positive control for this experiment, supernatants from Con A stimulated D10.G4.1 cells were used. It should be noted that native IL-10 shows a considerable amount of size heterogeneity with an apparent molecular mass of 27–50 kDa (Florentino, D. F., et al., 1989). This is thought to reflect the propensity of IL-10 to form homodimers. As described by Mosmann and colleagues (Mosmann, T. R., et al., 1990), the antibody used in these studies, SXC-1, does not recognize denatured IL-10 and only reacts with native IL-10. The antibody is toward an epitope shared by the native dimer form, this epitope is absent in the monomer. This property was reflected in the immunoblot, in which only non-denatured IL-10 was seen.

Figure 12:
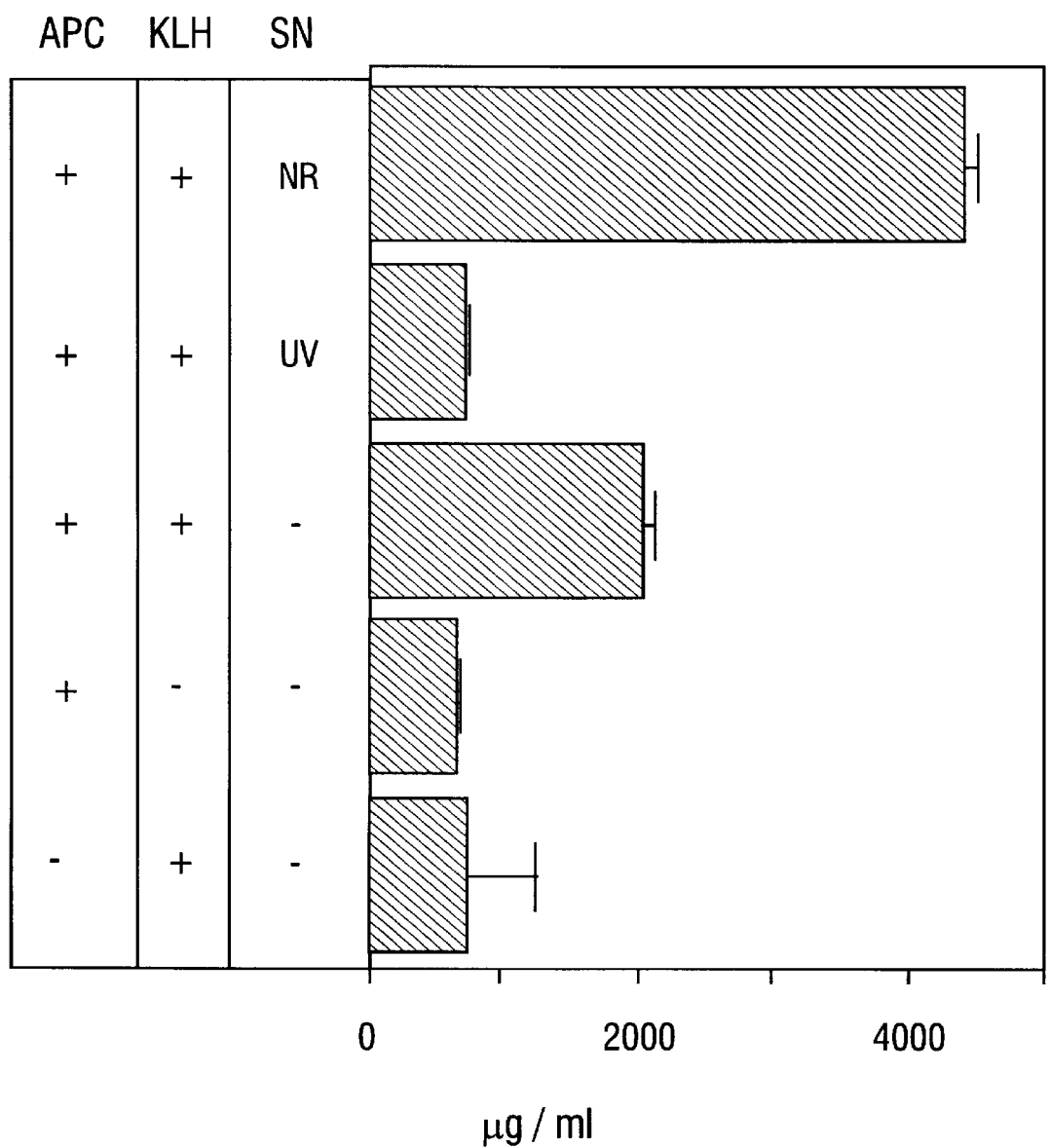
FIG. 12. IL-10 bioactivity in the supernatants from UV-irradiated keratinocytes. Th1 cells were cultured with and without antigen (KLH) and H-2$^d$ restricted antigen-presenting cells (APC) in the presence or absence of supernatants from UV-irradiated (UV) or mock-irradiated (NR) keratinocytes. The supernatants from these cultures were collected 18–24 h later and IFN-γ secretion was measured by ELISA.

Supernatants from UV-Irradiated keratinocytes Contain IL-10 bioactivity. To determine whether the IL-10-like molecule that was released in the supernatants of UV-irradiated keratinocytes has IL-10 bioactivity, the ability of these supernatants to suppress IFN-γ production by antigen-stimulated Th1 cells was measured. Supernatants from non-irradiated or UV-irradiated keratinocytes were added to cultures containing normal Balb/c spleen cells, HDK-1 cells, and antigen. The data from a representative experiment are presented in FIG. 12. When the HDK-1 cells were incubated with antigen-presenting cells but no antigen, or with antigen in the absence of antigen-presenting cells, little or no IFN-γ was released by the cells. When the antigen was presented to the HDK-1 cells by H-2$^d$ compatible antigen-presenting cells IFN-γ was produced. Addition of 20 µg of supernatant protein from the UV-irradiated keratinocytes completely suppressed IFN-γ production by the antigen-stimulated Th1 cells. Addition of an equal amount of protein from the non-irradiated keratinocytes had no suppressive effect. Indeed, in this particular experiment IFN-γ production was enhanced when the supernatant from the non-irradiated keratinocytes was added. The production of IFN-γ by the non-irradiated keratinocytes cannot explain this observation, since there was no detectable IFN-γ (<125 pg/ml by ELISA) in the supernatants from either the UV- or the non-irradiated keratinocytes.

EXAMPLE 12

Monoclonal Anti-IL-10 Blocks the Suppressive Effects of Supernatants from UV-Irradiated Keratinocytes and Partially Inhibits the Suppressive Effects of Total-Body UV-Irradiation This example describes the effects of blocking IL-10 bioactivity with monoclonal anti-IL-10 antibodies in vitro and in vivo.

Monoclonal Anti-IL-10 Blocks the Suppressive Effects of Supernatants from UV-Irradiated Keratinocytes. We next wanted to determine whether treating the UV-induced, keratinocyte-derived suppressive cytokine with anti-IL-10 monoclonal antibody would abrogate its suppressive activity. Twenty µg of supernatant protein from the UV-irradiated keratinocytes was incubated with 10 µg/ml of SXC-1 and incubated for 1 h. Goat anti-rat IgM was then added, and immune complexes were precipitated with protein A-agarose-coated beads. As a control, the supernatant was treated with an irrelevant isotype-matched antibody (anti-B220), incubated with goat anti-rat IgM, and precipitated with protein A. The effect that injecting these supernatants had on DTH to alloantigens was then measured, and data from a representative experiment are shown in Table 12.

TABLE 12

Anti-IL-10 Monoclonal Antibody Abrogates the Induction of Suppression by Supernatants from UV-Irradiated Keratinocytes

| Treatment[a] | ΔFootpad Swelling[b] | Specific Swelling[c] | % Suppression[d] | p[e] |
|---|---|---|---|---|
| Negative control | 6 ± 5 | — | | |
| Positive Control | 28 ± 6 | 22 | 0 | |
| UV-SN | 19 ± 6 | 13 | 41 | 0.007 |
| UV-SN + anti-IL-10 antibody | 31 ± 12 | 25 | 0 | 0.60 |
| UV-SN + control antibody | 18 ± 5 | 12 | 46 | 0.024 |

[a]BALB/c mice were injected with 20 µg of supernatant protein from UV-irradiated keratinocyte cultures that were treated with anti-IL-10 or isotype-matched control monoclonal antibody. Five days later, the mice were sensitized with alloantigen. DTH was measured 7 days later. Positive control refers to mice that were not injected with any supernatant but were sensitized and challenged. Negative control animals were not sensitized but were challenged.
[b]Units = mm × 10$^{-2}$ (five mice per group)
[c]The background swelling found in non-sensitized mice was subtracted from the swelling found in the sensitized groups.
[d]% suppression = [1 − (specific footpad swelling experimental/specific footpad swelling of the positive control)] × 100.
[e]p values determined by two-tailed Student's t-test, positive control vs. experimental groups.

Compared with the positive control (normal immunized mice), injecting supernatants from UV-irradiated keratinocytes significantly suppressed (41% suppression; p=0.007; Student's t-test) the induction of DTH. Treating the supernatant with anti-IL-10 antibody eliminated all the suppressive activity. Treating the supernatant with the irrelevant isotype-matched control antibody had no effect. The observed suppression was similar to that seen when untreated supernatant was injected (46% suppression; p=0.024; Student's t-test).

Monoclonal Anti-IL-10 Inhibits the Suppressive Effects of Total-Body UV-Irradiation. We next measured the effect of injecting monoclonal anti-IL-10 on the suppression caused by UV radiation. C3H/HeN mice were exposed to 15 kJ/m$^2$ of UV radiation and, 4 and 24 h later, were injected with 100 μg of rat anti-mouse IL-10. Five days later the animals were sensitized with alloantigen, and 7 days later, DTH to the alloantigen was measured as described above. The data from this experiment are found in Table 13.

TABLE 13

Anti-IL-10 Monoclonal Antibody Partially Blocks the Induction of Immunosuppression Following Total-Body UV Exposure

| Treatment[a] | ΔFootpad Swelling[b] | Specific Swelling[b] | % Suppression[b] | p[b] |
|---|---|---|---|---|
| Negative control | 15 ± 5 | 0 | | |
| Positive Control | 34 ± 8 | 19 | 0 | |
| UV | 18 ± 7 | 3 | 84 | 0.001 |
| UV + anti-IL-10 | 26 ± 3 | 11 | 42 | 0.013 |
| UV + Normal Rat Serum | 19 ± 6 | 4 | 79 | 0.001 |

[a]C3H mice were exposed to UV radiation (15 kJ/m$^2$) and 4 and 18 h later injected with 100 μg of rat-anti-mouse IL-10 or normal rat serum. Five days after UV exposure, the mice were sensitized with alloantigen. Seven days later DTH was measured. Positive control refers to mice that were not injected with any supernatant but were sensitized and challenged. Negative control animals were not sensitized but were challenged.
[b]See footnotes to Table 12.

UV exposure suppressed DTH to alloantigen (84% p<0.001 Students t-test). Injecting UV-irradiated mice with monoclonal anti-IL-10 partially reversed the suppressive effect (42% suppression). Injecting the UV-irradiated animals with normal rat serum had no effect. The observed suppression was similar to that seen in mice exposed only to UV radiation.

The UV-induced production of IL-10 by keratinocytes may be the first step in a cascade, and IL-10 release may induce other cells within the epidermis to release other suppressive cytokines such as TNF-α and perhaps tumor growth factor-beta (TGF-β). This may explain why Yoshikawa and Streilein were able to block the UV-induced immunosuppression with antibodies to TNF-α, while we found no TNF-α in our suppressive supernatants (Yoshikawa, T. et al., 1990). The release of multiple keratinocyte-derived suppressive cytokines in vivo may also explain the observation made here that neutralizing antibodies against IL-10 could totally block the suppressive activity of the supernatants from the UV-irradiated keratinocytes (Table 1) but only partially block the immunosuppression seen following UV exposure in vivo (Table 2). Undoubtedly other suppressive factors such as contra-IL-1, TNF-α, TGF-β (Akhurst, R. J. et al., 1988), and prostaglandins (Chung, H. T. et al., 1986), are being released by the UV-irradiated epidermal cells, and these factors probably work in concert to suppress DTH. However, the fact that antibodies against IL-10 can reduce the observed suppression by at least one-half indicates a prominent role for keratinocyte-derived IL-10 in the induction of suppression.

Similar to the situation found with most of the other keratinocyte-derived cytokines, keratinocyte activation is clearly necessary to cause the release of IL-10. Although we did see baseline levels of IL-10 mRNA expression in the non-irradiated keratinocytes, no IL-10 was found in supernatants of the mock-irradiated cells by Western analysis nor was any IL-10 bioactivity present in these supernatants. It is of interest to note that although IL-10 mRNA was unregulated at 24 h in mock-irradiated keratinocytes, no IL-10 protein was found in the supernatant. This finding is not too surprising since keratinocytes are known to constitutively produce mRNA for other cytokines without actively secreting the cytokine. IL-1β is a prominent example. Kupper et al., (1987), reported that IL-1α and β mRNA is up-regulated in human keratinocyte following UV exposure but only IL-1α is found in the supernatant. Mizutani et al. (1991), have recently found that keratinocytes lack the enzymes required to process the 31 kDa pro-IL-1β to the active 17 kDa form, hence up-regulated message expression without protein secretion. Furthermore, they point out that mRNA for TGF-β and TNF-α is often up-regulated in keratinocytes without concordant biological activity being found in the supernatant. Similarly, the present inventors find basal levels of IL-10 mRNA in non-irradiated keratinocytes and enhanced IL-10 mRNA expression in mock-irradiated keratinocytes at 24 h without finding the protein in the supernatant. These findings suggest that the release of biologically active IL-10 by keratinocytes requires some sort of processing step, a step activated by UV-exposure. Other signals besides UV radiation may stimulate keratinocytes to produce IL-10. A recent report by Enk and Katz suggest that contact allergens can activate epidermal cells to produce IL-10 (Enk et al., 1992). mRNA for IL-10 was enhanced in murine epidermal cells following the application of contact allergens. Activity was enhanced 4 h after application and reached peak levels at 12 h. Immunoprecipitation with IL-10 monoclonal antibody showed that the haptenated epidermal cells released IL-10. In addition, the cell responsible for the release of IL-10 was the keratinocyte. Thus, these data indicate that contact allergens can induce keratinocytes to release IL-10. Furthermore, the present inventors have recently reported that psoralen and UVA (PUVA) treatment of keratinocytes caused the release of a factor that also suppressed DTH to alloantigens (Aubin, F. et al., 1991). Whether this keratinocyte-derived factor is IL-10 remains to be seen, but these data suggest that PUVA-treatment may stimulate keratinocytes to release IL-10. Finally, others have shown that treating mouse skin with chemical carcinogens or tumor promoters induces a systemic suppression of delayed-in-time hypersensitivity reactions. (Halliday, G. M. et al., 1987; Kodari, E. et al., 1991). The data presented here indicates that keratinocyte-derived IL-10 explains the induction of systemic suppression following treatment of the skin with chemical carcinogens or tumor promoters.

EXAMPLE 13

Inactive Recombinant IL-10 Fails to Mimic the Immune Suppressive Effect of Supernatants from UV-irradiated Keratinocytes The present example concerns the ability of recombinant IL-10 to mimic the immune suppressive effect that is observed following the injection of the supernatant from UV-irradiated keratinocytes into mice. Recombinant mouse IL-10 was purchased from PharMingen (San Diego, Calif.). Normal mice were then injected with different doses of rIL-10, 1, 5, 10, 50 units per mouse. Five days later the mice were immunized with allogeneic histocompatibility antigens, and 7 days later the ability of these mice to mount a delayed-type hypersensitivity reaction was measured. No immune suppression was found in the mice injected with rIL-10. This result was inconsistent with the reported function of IL-10 (Florentino et al. 1989, *J. Exp. Med.*, 170:2081–2095). However, the activity of the rIL-10 in the standard IL-10 bioassay was tested (inhibition of interferon gamma production by antigen-activated Th1 cells) as described in Example 11 and found to be inactive. Because the material purchased from PharMingen is inactive no conclusion can be made concerning the ability of recombinant IL-10 to mimic the immune suppressive effect.

EXAMPLE 14

Antibodies to IL-10 But Not TNP-α Block UV-Induced Suppression of Delayed-Type Hypersensitivity to Allogeneic Histocompatibility Antigens This example describes whether other keratinocyte-derived cytokines are involved in the induction of immune suppression following UV exposure. Keratinocytes release many cytokines after UV exposure, and other studies have suggested that TNF-α is involved in suppressing contact hypersensitivity following UV exposure (Yoshikawa and Streilein, 1990, *Regional Immunology* 3:139). In the present example, mice were exposed to UV radiation, and 4 and 24 hours later injected with antibodies against either IL-10 or TNF-α. Five days following exposure, the animals were sensitized with antigen, and 7 days later DTH was measured (see Table 14).

TABLE 14

Antibodies to IL-10 but not TNF-α block UV-induced suppression of Delayed-type hypersensitivity to allogeneic histocompatibility antigens.

| | Treatment[a] | ΔFootpad Swelling[b] | Specific Swelling[c] | % Suppression[d] | p[e] |
|---|---|---|---|---|---|
| Exp. #1 | Negative control | 6 ± 5 | — | | |
| | Positive Control | 33 ± 12 | 27 | — | |
| | UV | 13 ± 7 | 7 | 74 | 0.001 |
| | UV + anti-IL-10 | 28 ± 7 | 22 | 19 | 0.132 |
| | UV + rat serum | 19 ± 10 | 13 | 52 | 0.02 |
| | UV + anti-TNF-α | 20 ± 8 | 14 | 48 | 0.02 |
| | UV + anti-BSA | 22 ± 8 | 16 | 40 | 0.02 |
| Exp. #2 | Negative control | 4 ± 3 | — | | |
| | Positive control | 19 ± 6 | 15 | — | |
| | UV | 10 ± 6 | 6 | 60 | 0.01 |
| | UV + anti-IL-10 | 14 ± 6 | 10 | 33 | 0.1 |
| | UV + rat serum | 5 ± 4 | 1 | 93 | 0.001 |
| | UV + anti-TNF-α | 8 ± 3 | 4 | 74 | 0.001 |
| | UV + anti-BSA | 9 ± 6 | 5 | 63 | 0.004 |

[a]Mice were exposed to UV radiation and 4 and 24 hours later injected with rat anti-IL-10 (SXC-1, 100 μg), rabbit anti-TNF-α (Genzyme, 2 × 10$^4$ neutralizing units), normal rat serum (100 μg), or rabbit anti-BSA (Sigma Chemicals, 100 μg). Five days following UV exposure the mice were injected with 5 × 10$^7$ allogeneic spleen cells. Negative control refers to mice that were not immunized but were challenged. Positive control refers to mice that were immunized and challenged. In Experiment 1, BALB/c mice were exposed to UV radiation (15 kJ/m$^2$) and immunized with C3H/HeN spleen cells. Experiment 2, C3H/HeN mice were exposed to UV radiation (15 kJ/m$^2$) and immunized with BALB/c spleen cells. There were 10 mice per group in Experiment 1 and 5 per group in Experiment 2.
[b]Units = mm × 10$^{-2}$.
[c]The background swelling found in the non-sensitized mice was subtracted from the swelling found in sensitized animals.
[d]% suppression = [1 − (specific footpad swelling experimental/specific footpad swelling of the positive control)] × 100.
[e]P values determined by the two-tailed Student's T-test, positive control versus experimental groups. A representative experiment is shown, this experiment has been repeated 5 times with similar results.

As expected, total body UV exposure suppressed the ability of the mice to generate a DTH reaction. Injecting anti-IL-10 into these mice totally reversed the induction of immune suppression as there was no statistical difference between the positive control and the group injected with anti-IL-10 antibodies. Injecting normal rat serum (the anti-IL-10 is a rat anti-mouse monoclonal), had no suppressive effect. On the other hand, when UV-irradiated mice were injected with either anti-TNF or control anti-BSA antibodies, no inhibition of suppression was observed (P<0.02). Thus these data indicate that IL-10 and not TNF-α is involved in the induction of immune suppression following UV exposure in vivo. These data strongly suggest that only IL-10 is involved in suppressing DTH following UV exposure.

EXAMPLE 15

UV Suppressor Cells are Th2 Cells

Figure 13:
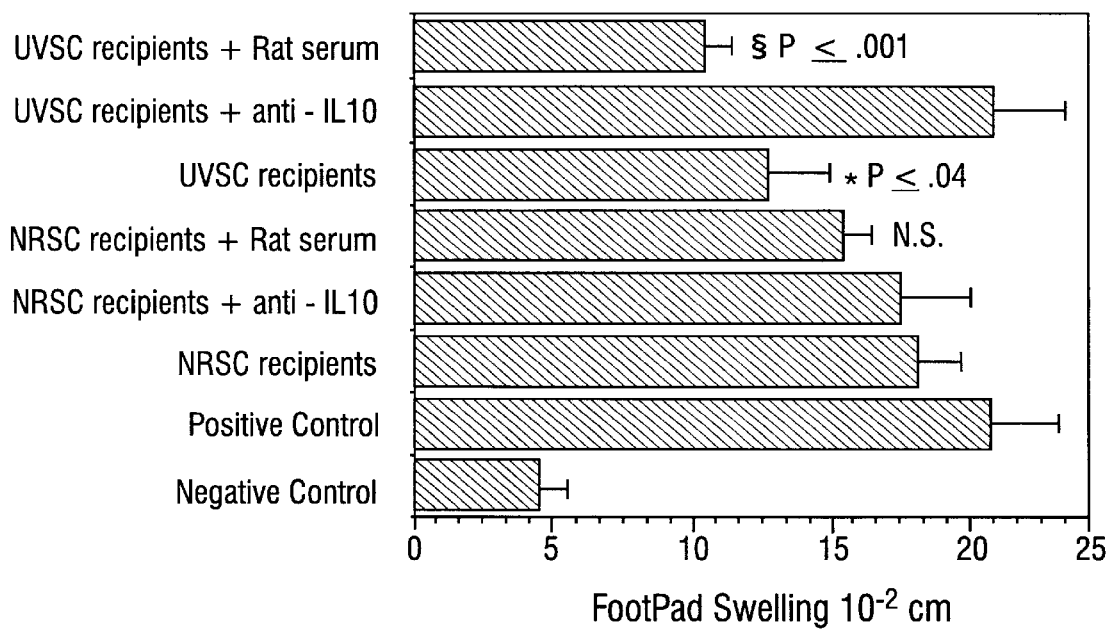
FIG. 13 demonstrates that UV suppressor cells are Th2 cells. Mice were exposed to UV radiation and sensitized with alloantigen. Seven days later DTH was measured in these mice and found to be suppressed. The spleens of these animals were removed, single cell suspension prepared and injected into a group of normal syngeneic mice. These mice were then injected with alloantigen and their DTH response was measured 7 days later. NRSC=spleen cells from normal mice, UVSC=spleen cells from UV-irradiated mice.

This example addresses the role of IL-10 in suppressing immune reactions following UV irradiation. Recently it was discovered that there are at least two different subsets of CD4+ helper cells. The first subset, T helper 1 cells (Th1), produces interleukin 2, interferon-gamma and lymphotoxin following antigen stimulation and appears to consist of cells involved in providing help for cellular immune reactions such as DTH. The second subset, Th2 cells, makes interleukins 4, 5, 6 and 10 following antigenic stimulation and provides help for antibody production. Furthermore, there appears to be a cross regulation of immune responses by Th1 and Th2 cells. Interferon-gamma blocks the proliferation of Th2 cells, thus, preventing the generation of help for antibody reactions, and the IL-10 produced by Th2 cells blocks the secretion of interferon-gamma by Th1 cells, thus, suppressing the development of DTH. The present inventors have previously observed that the suppressor cells found in UV-irradiated mice were CD4+ cells and, therefore, performed the following experiment to examine if the suppressor cells were in actuality Th2 cells, and suppressed DTH by virtue of their IL-10 production. Mice were exposed to UV radiation and sensitized with alloantigen. Seven days later DTH was measured in these mice and found to be suppressed. The spleens of these animals were removed, single cell suspension prepared and injected into a group of normal syngeneic mice. These mice were then injected with alloantigen and their DTH response was measured 7 days later. The data from this experiment is presented in FIG. 13, and Table 15, and indicate the following: (1) injecting spleen cells from normal mice (NRSC recipients) did not suppress DTH in the recipient animals, (2) Injecting spleen cells from UV-irradiated mice resulted in a significant suppression of DTH in the recipient animals (UVSC recipients). Injecting anti-IL-10 antibody into recipients that received the UVSC totally reversed the suppressive effect (UVSC+anti-IL-10). Injecting normal rat serum into mice that were injected with the UVSC had no effect, the suppression seen in these mice was similar to that seen in mice injected with only the UVSC. These data indicate that the UV-induced suppressor cells mediate their immunosuppressive effects by releasing IL-10, thus the cells appear to be Th2 cells. This example supports the contention that IL-10 is the essential cytokine for induction and maintaining immune suppression after UV exposure.

TABLE 15

UV Suppressor Cells are Th2 Cells

| Samples | Mean | S.D. | S.E.M. | Std. Error |
| --- | --- | --- | --- | --- |
| 1 Negative control | 4.3 | 3.4 | 1.0 | 1.0 |
| 2 Positive control | 21.1 | 7.2 | 2.6 | 2.6 |
| 3 NRSC recipients | 18.5 | 4.8 | 1.7 | 1.7 |
| 4 NRSC recipients + anti-IL-10 | 18.0 | 7.0 | 2.5 | 2.5 |
| 5 NRSC recipients + rat serum | 16.0 | 3.2 | 1.1 | 1.1 |
| 6 UVSC recipients | 13.3 | 6.5 | 2.3 | 2.3 |
| 7 UVSC recipients + anti-IL-10 | 21.6 | 7.6 | 2.7 | 2.7 |
| 8 UVSC recipients + rat serum | 11.1 | 3.0 | 1.0 | 1.0 |

Citations within the specification in addition to the following list are incorporated in pertinent part by reference herein for the reasons cited.

REFERENCES

Akhurst, R. J. et al., 1988. Localized production of TGF-β mRNA in tumor promoter-stimulated mouse epidermis. *Nature.* 331:363.

Ansel, J. C., et al., 1988. The expression and modulation of IL-1a in murine keratinocytes. *J. Immunol* 140:2274.

Ansel, J. et al., 1990. Cytokine modulation of keratinocyte cytokines. *J. Invest. Dermatol.* 94:101.

Aubin, F. et al., 1991. Activation of keratinocytes with psoralen plus UVA radiation induces the release of soluble factors that suppress delayed and contact hypersensitivity. *J. Invest. dermatol.* 97:995.

Cherwinski, H. et al., 1987. Two types of mouse helper T. clones. III. Further differences in lymphokine synthesis between Th1 and Th2 clones. *J. Exp. Med.* 166:1224.

Chung, H. T. et al., 1986. Involvement of prostaglandins in the immune alterations caused by the exposure of mice to ultraviolet radiation. *J. Immunol.* 137:2478.

De Fabo et al., 1983. Mechanism of immune suppression by ultraviolet irradiation in vivo. I-Evidence for the existence of a unique photoreceptor in skin and its role in photoimmunology. *J. Exp. Med.* 157:84.

Dunnett C., 1985: A multiple comparison procedure for comparing several treatments with a control. J. Am. Stat. Assoc. 50:1096–1124.

Enk, A. H. et al., 1992. Identification and induction of keratinocyte-derived interleukin-10. *J. Invest. Dermatol.* 98:578.

Evertt et al., 1966. Penetration of epidermis by ultraviolet rays. *Photochem. Photobiol.* 5:533.

Fidler, I. J., 1973. The relationship of embolic homogeneity, number, size and viability to the incidence of experimental metastases. Eur J Cancer 9:223.

Fisher M. S., Kripke M. L., 1982: Suppressor T lymphocytes control the development of primary skin cancers in ultraviolet-irradiated mice. *Science* 216:1133–1134.

Florentino, D. F. et al., 1989. Two types of mouse helper cells. IV. Th2 clones secrete a factor that inhibits cytokine production by $Th_1$ clones. *J. Exp. Med.* 170:2081.

Florentino, D. F. et al., 1991. IL-10 acts on the antigen-presenting cell to inhibit cytokine production by Th1 cells. *J. Immunol.* 146:3444.

Gahring L. C., et al., 1984. The Effect of UV Radiation On The Production of ETAF:IL-1 in vivo and in vitro. Proc. Natl. Acad. Sci. USA 81:1198–1202.

Gazzinelli, R. T. et al., 1992. IL-10 inhibits parasite killing and nitrogen oxide production by IFN-γ-activated macrophages. *J. Immunol.* 148:1792.

Gottlieb, R. A. et al., 1989. Synthetic peptide corresponding to a conserved domain of the retroviral protein p15E blocks IL-1-mediated signal transduction. *J. Immunol.* 142:4321.

Greene et al., 1979: Impairment of antigen-presenting cell function by UV radiation. Proc. Natl. Aca. Sci USA 76:6591–6595.

Halliday, G. M. et al., 1987. Sensitization through carcinogen-induced Langerhans cell-deficient skin activates specific long-lived suppressor cells for both cellular and humoral immunity. *Cell. Immunol.* 109:206.

Harriott-Smith, T. G. et al., 1988. Suppression of contact hypersensitivity by short-term ultraviolet irradiation: I Immunosuppression by serum from irradiated mice. Clin. Exp. *Immunol.* 71:144.

Harriott-Smith T. G., Halliday W. J., 1986. Circulating suppressor factors in mice subjected to ultraviolet irradiation and contact hypersensitivity. *Immunology* 57:207–211, 1986.

Jeevan, A. et al., 1992. Supernatants from UV-irradiated keratinocytes decrease the resistance and delayed type hypersensitivity response to *Mycobacterium Bovis* BCG in mice and impair the phagocytic ability of macrophages. *Photodermatology, Photolimmunology & Photomedicine.* 9:255–263.

Jerne N. K., Nordin A. A., 1963. Plaque formation in agar by single antibody producing cells. *Science.* 140:405–406.

Kim, T. Y. et al., 1990. Immunosuppression by factors released from UV-irradiated epidermal cells: selective effects on the generation of contact and delayed hypersensitivity after exposure to UVA or UVB radiation. *J. Invest. Dermatol.* 94:26.

Klein J. et al., 1986. Participation of H-2 regions in heart transplant rejection. Transplantation 22:384.

Kock, A. et al., 1990. Human keratinocytes are a source for tumor necrosis factor α: evidence for synthesis and release upon stimulation with endotoxin or ultraviolet light. *J. Exp. Med.* 172:1609.

Kodari, E. et al., 1991. Induction of suppressor T cells and inhibition of contact hypersensitivity in mice by TPA and its analogs. *J. Invest. Dermatol.* 96:864.

Korngold, R., Sprent J., 1985. Surface markers of T cells causing lethal graft versus host disease to class I vs. class II H-2 differences. *J Immunol.* 135:3004.

Kripke, M. L. 1984. Immunologic unresponsiveness induced by UV radiation. *Immunol. Rev.* 80:87.

Kripke M. L., 1977. Latency, histology, and antigenicity of tumors induced by UV light in three inbred mouse strains. Cancer Res 37:1395.

Kripke, 1974. Antigenicity of murine skin tumors induced by UV light. *J. Natl. Cancer Inst.* 53:1333.

Kripke et al., 1977. In vivo immune responses of mice during carcinogenesis. JNCI 59:1227–1230.

Krutmann, J. et al., 1990. Epidermal cell-contra-interleukin 1 inhibits human accessory cell function by specifically blocking interleukin 1 activity. *Photochem. Photobiol.* 52:738.

Kupper, T. S., et al. Interleukin 1 gene expression in cultured human keratinocytes is augmented by ultraviolet irradiation. *J. Clin. Invest.* 80:430.

Kupper, T., and D. R. Green. 1984. Immunoregulation after thermal injury: sequential appearance of I-J+, Lyt 1 T suppressor inducer cells and Lyt 2 T suppressor effector cells following thermal trauma in mice. *J. Immunol.* 135:3047.

Laemmli, U. K. 1970. Cleavage of structural proteins during the assembly of the head of the bacteriophage T4. *Nature* 27:680.

Lau H., et al., 1983. Pancreatic islet allograft prolongation by donor-specific blood transfusions treated with UV irradiation. *Science* 221:754.

Lau H., et al., 1984. Reemtsma K., Hardy M. A. Prolongation rat islet allograft survival by direct UV irradiation of the graft. *Science* 223:607.

Liew, F. Y. 1982. Regulation of delayed type hypersensitivity. VI Antigen-specific suppressor T cells and suppressor factor for DTH to histocompatibility antigens. Transplantation 33:69.

Luger, T. A. et al., 1989. Epidermal cell derived cytokines. skin immune system. Bos, J. D. CRC Press, Boca Raton, Fla. 257.

Mishell R. I., Dutton R. W., 1967. Immunization of dissociated spleen cell cultures from normal mice. *J. Exp. Med.* 126, 423–442.

Mizutani, H. et al., 1991. Human keratinocytes produce but do not process pro-Interleukin-1 (IL-1) Beta. Different strategies of IL-1 production and processing in monocytes and keratinocytes. *J. Clin. Invest.* 87:1066.

Molendijk et al., 1987. Suppression of delayed-type hypersensitivity to histocompatibility antigens by ultraviolet radiation. *Immunology.* 62:299.

Moore, K. W. et al., 1990. Homology of cytokine synthesis inhibitory factor (IL-10) to the Epstein-Barr virus gene BCRFI. *Science.* 248:1230.

Mosmann, T. R. et al., 1990. Isolation of monoclonal antibodies specific for IL-4, IL-5, IL-6, and a new Th2 specific cytokine (IL-10), cytokine synthesis inhibitory factor, by using a solid phase radioimmunoadsorbent assay. *J. Immunol.* 145:2938.

Mosmann, T. R., 1991. Regulation of Immune responses by T cells with different cytokine secretion phenotypes: Role of a new cytokine, cytokine synthesis inhibitory factor (IL10). *Int. Arch. Allergy and Appl. Immunol.* 94:110.

Noonan, F. P. et al., 1988. Cis-urocanic acid, a product formed by UVB irradiation of the skin, initiates an antigen presentation defect in splenic cells in vivo. *J. Invest. Dermatol.* 90:92.

Noonan et al., 1981. Suppression of contact hypersensitivity by UV radiation: An experimental model. Springer Semin. Immunopath. 4:293–2304.

Norbury, K. C. et al., 1977. In vitro reactivity of macrophages and lymphocytes from UV-irradiated mice. *J. Natl. Cancer Inst.* 59:1231.

Parish, C. R., 1972. The relationship between humoral and cell-mediated immunity. *Transplant. Rev.* 13:35.

Robertson B. et al., 1987. In vivo administration of IL-1 to normal mice decreases their capacity to elicit contact hypersensitivity responses: Prostaglandins are involved in this modification for the immune response. *J. Invest. Dermatol.* 88:380–387.

Ross J. A. et al., 1986. Ultraviolet-irradiated Urocanic acid suppresses delayed hypersensitivity to Herpes Simplex virus in mice. *J. Invest. Dermatol.* 87:630–633.

Ross, J. A. et al., 1988. Systemic administration of urocanic acid generates suppression of the delayed type hypersensitivity response to Herpes Simplex Virus in a murine model of infection. Photodermatology 5:9.

Schwarz T. et al., 1986. Inhibition of the induction of contact hypersensitivity by a UV-mediated epidermal cytokine. *J. Invest. Dermatol.* 87:289–291.

Schwarz, T. et al., 1987. UV-Irradiated epidermal cells produce a specific inhibitor of IL-1 activity. *J. Immunol.* 138:1457.

Shearer G. M., 1974. Cell-mediated cytotoxicity to trinitrophenyl-modified syngeneic lymphocytes. Eur. U. *Immunol.* 4:527–533.

Spellman, C. W. et al., 1977. Modification of immunological potential by ultraviolet radiation. I Immunological status of short-term UV-irradiated mice. Transplantation. 24:112.

Storb R., 1987. Critical issues in bone marrow transplantation. Transplant Proc. 19:2772.

Swartz, R. P, 1984. Role of UVB-induced serum factors in suppression of contact hypersensitivity in mice. *J. Invest. Dermatol.* 83:305.

Swartz, R. P. 1986. Suppression of DTH to UV radiation induced tumor cells with serum from UVB-irradiated mice. JNCI 76:1181.

Ullrich, S. E. et al., 1990. Suppression of the immune response to alloantigen by factors released from ultraviolet-irradiated keratinocytes. *J. Immunol.* 145:489.

Ullrich et al., 1986a. Suppression of the induction of delayed hypersensitivity reactions in mice by a single exposure to UV radiation. *Photochem. Photobiol.* 43:633.

Ullrich, 1986b. Suppression of the immune response to allogeneic histocompatibility antigen by a single exposure to UV radiation. Transplantation. 42:287.

Ullrich S. E. et al., 1986c. Suppressor lymphocytes induced by epicutaneous sensitization of UV-irradiated mice control multiple immunological pathways. *Immunology* 58:185.

Ullrich et al., 1988. Specific suppression of allograft rejection after treatment of recipient mice with UV radiation and allogeneic spleen cells. Transplantation. 46:115.

Ullrich S. E. et al., 1984. Mechanisms in the suppression of tumor rejection produced in mice by repeated UV irradiation. *J Immunol* 133:2786.

Ullrich, S. E. et al., 1991. The role of keratinocyte-derived suppressive cytokines in the systemic immunosuppression induced by ultraviolet B radiation. *Trends in Photochemistry and Photobiology.* 2:137.

Urbach, 1978. Evidence and epidemiology of UV-induced carcinogenesis in man. *Natl. Cancer Inst. Monogr.* 50:5.

Yoshikawa, T. et al., 1990. Tumor necrosis factor-alpha and ultraviolet light have similar effects on contact hypersensitivity in mice. *Regional Immunol.* 3:139.

Yuspa S. H. et al., 1980. A survey of transformation markers in differentiating epidermal cell lines. *Cancer Research* 40:4694–4703.

What is claimed is:

1. A method for inhibiting GVHD in a bone marrow recipient, comprising:
   (a) administering to a prospective bone marrow cell donor an amount of a isolated glycoprotein preparation effective to inhibit GVHD having the following properties:
      (i) binding affinity for concanavalin A-agarose;
      (ii) a reduced binding affinity for concanavalin A-agarose in the presence of α-D-mannopyranoside;
      (iii) a suppressive effect on delayed-type hypersensitivity without having an inhibitory effect on mammalian antibody production; and
      (iv) isolatable from a culture of PAM 212 epidermal cells subjected to UVB-irradiation;
   (b) sensitizing the prospective donor thereafter to alloantigens of a prospective bone marrow cell recipient; and
   (c) transplanting bone marrow cells from the prospective donor to the prospective bone marrow cell recipient.

2. The method according to claim 1, wherein the glycoprotein preparation is isolated by a process having the steps of:
   (a) irradiating a plurality of PAM 212 mammalian epidermal cells with UVB-irradiation in an amount of about 10 J/m$^2$ to about 200 J/m$^2$;
   (b) incubating said cells in a nutrient medium;
   (c) separating said glycoprotein preparation by contacting said nutrient medium with a concanavalin A-agarose affinity matrix; and
   (d) eluting said glycoprotein preparation from said matrix with α-D-mannopyranoside.

3. The method according to claim 1, wherein said administering comprises parenteral administration.

4. The method according to claim 3, wherein said administering comprises intravenous administration.

5. The method according to claim 4, wherein said sensitizing comprises the parenteral administration of a sample bearing said alloantigens.

6. The method according to claim 4, wherein said sensitizing comprises the subcutaneous administration of a sample bearing said alloantigens.

* * * * *

SEQUENCE LISTING (1) GENERAL INFORMATION:

(iii) NUMBER OF SEQUENCES: 3

(2) INFORMATION FOR SEQ ID NO: 1:

-continued (i) SEQUENCE CHARACTERISTICS:
    (A) LENGTH: 20 base pairs
    (B) TYPE: Nucleic Acid
    (C) STRANDEDNESS: Single
    (D) TOPOLOGY: Linear (ii) MOLECULE TYPE: Oligonucleotide (iii) SEQUENCE DESCRIPTION: SEQ ID NO: 1:

CGGGAAGACA ATAACTGCAC                                           20

(2) INFORMATION FOR SEQ ID NO:2:

(i) SEQUENCE CHARACTERISTICS:
        (A) LENGTH: 20 base pairs
        (B) TYPE: Nucleic acid
        (C) STRANDEDNESS: Single
        (D) TOPOLOGY: Linear (ii) MOLECULE TYPE: Oligonucleotide (iii) SEQUENCE DESCRIPTION: SEQ ID NO:2:

CAGGCAGAGA AGCATGGCCC                                           20

(2) INFORMATION FOR SEQ ID NO:3:

(i) SEQUENCE CHARACTERISTICS:
        (A) LENGTH: 20 base pairs
        (B) TYPE: Nucleic acid
        (C) STRANDEDNESS: Single
        (D) TOPOLOGY: Linear (ii) MOLECULE TYPE: Oligonucleotide (iii) MOLECULE TYPE: Oligonucleotide (iv) SEQUENCE DESCRIPTION: SEQ ID NO:3:

ACTGCATAGA AGCATACATG                                           20